(12) United States Patent  
Smirnov et al.

(10) Patent No.: US 8,906,609 B1
(45) Date of Patent: Dec. 9, 2014

(54) LABEL-FREE BIOMOLECULE SENSOR BASED ON SURFACE CHARGE MODULATED IONIC CONDUCTANCE

(75) Inventors: Sergei Smirnov, Las Cruces, NM (US); Xian Wang, Las Cruces, NM (US)

(73) Assignee: Arrowhead Center, Inc., Las Cruces, NM (US)

( * ) Notice: Subject to any disclaimer, the term of this patent is extended or adjusted under 35 U.S.C. 154(b) by 547 days.

(21) Appl. No.: 12/723,351

(22) Filed: Mar. 12, 2010

Related U.S. Application Data

(63) Continuation-in-part of application No. 11/918,187, filed on Nov. 30, 2007, now abandoned, which is a continuation-in-part of application No. 11/527,845, filed on Sep. 26, 2006, now abandoned.

(60) Provisional application No. 60/720,790, filed on Sep. 26, 2005, provisional application No. 61/237,926, filed on Aug. 28, 2009.

(51) Int. Cl.
  *C12Q 1/68* (2006.01)
  *C12M 1/00* (2006.01)
  *C12M 1/34* (2006.01)
  *C12M 3/00* (2006.01)

(52) U.S. Cl.
  USPC .... 435/6.1; 435/283.1; 435/287.1; 435/287.2

(58) Field of Classification Search
  CPC .................. C12Q 2563/155; C12Q 2565/631; C12Q 1/6816; C12Q 1/6874; G01N 33/48721
  See application file for complete search history.

(56) References Cited

U.S. PATENT DOCUMENTS

| | | |
|---|---|---|
| 4,661,235 A | 4/1987 | Krull et al. |
| 4,713,347 A | 12/1987 | Mitchell et al. |
| 4,722,771 A | 2/1988 | Textor et al. |
| 5,034,506 A | 7/1991 | Summerton et al. |
| 5,124,172 A | 6/1992 | Burrell et al. |
| 5,142,047 A | 8/1992 | Summerton et al. |
| 5,166,315 A | 11/1992 | Summerton et al. |
| 5,185,444 A | 2/1993 | Summerton et al. |
| 5,204,239 A | 4/1993 | Gitler et al. |
| 5,368,712 A | 11/1994 | Tomich et al. |
| 5,472,881 A | 12/1995 | Beebe et al. |
| 5,506,337 A | 4/1996 | Summerton et al. |
| 5,521,063 A | 5/1996 | Summerton et al. |
| 5,688,642 A | 11/1997 | Chrisey et al. |

(Continued)

FOREIGN PATENT DOCUMENTS

| | | |
|---|---|---|
| WO | WO 97/44651 | 11/1997 |
| WO | WO-03/102234 A1 | 12/2003 |

(Continued)

OTHER PUBLICATIONS

Maehashi et al, Japan. Journ. Appl. Phys., vol. 43, pp. L1558-L1560, published Nov. 12, 2004.*

(Continued)

*Primary Examiner* — Robert T. Crow
(74) *Attorney, Agent, or Firm* — Janeen Vilven; Deborah A. Peacock; Peacock Myers, P.C.

(57) ABSTRACT

The present invention provides for the detection of biochemical analytes by measuring variations in ionic conductance resulting from the hybridization of a biological analyte (e.g. oligonucleotides) with a capturing element immobilized on a membrane substrate having nano-sized pores.

6 Claims, 11 Drawing Sheets

(56) References Cited

U.S. PATENT DOCUMENTS

| | | | |
|---|---|---|---|
| 5,698,685 | A | 12/1997 | Summerton et al. |
| 5,789,167 | A | 8/1998 | Konrad |
| 5,795,782 | A | 8/1998 | Church et al. |
| 5,837,446 | A | 11/1998 | Cozzette et al. |
| 5,846,744 | A | 12/1998 | Athey et al. |
| 6,139,713 | A | 10/2000 | Masuda et al. |
| 6,362,002 | B1 | 3/2002 | Denison et al. |
| 6,368,875 | B1 | 4/2002 | Geisberg et al. |
| 6,426,231 | B1 | 7/2002 | Bayley et al. |
| 6,476,409 | B2 | 11/2002 | Iwasaki |
| 6,528,167 | B2 | 3/2003 | O'Gara |
| 6,627,067 | B1 | 9/2003 | Branton et al. |
| 6,638,760 | B1 | 10/2003 | Chen et al. |
| 6,649,418 | B1 | 11/2003 | Geisberg |
| 6,846,654 | B1 | 1/2005 | Blackburn et al. |
| 6,872,527 | B2 | 3/2005 | Gerdes et al. |
| 6,924,023 | B2 | 8/2005 | Ohkura et al. |
| 6,927,070 | B1 | 8/2005 | Bayley et al. |
| 6,952,651 | B2 | 10/2005 | Su |
| 7,005,264 | B2 | 2/2006 | Su et al. |
| 7,014,992 | B1 | 3/2006 | Kayyem et al. |
| 7,052,616 | B2 | 5/2006 | Fonash et al. |
| 7,067,253 | B1 | 6/2006 | Bertling et al. |
| 7,077,939 | B1 | 7/2006 | Crooks et al. |
| 7,087,387 | B2 | 8/2006 | Gerdes et al. |
| 7,195,697 | B2 | 3/2007 | Clausen |
| 7,355,216 | B2 | 4/2008 | Yang et al. |
| 7,374,944 | B2 | 5/2008 | Thompson et al. |
| 7,410,564 | B2 | 8/2008 | Flory |
| 7,518,010 | B2 | 4/2009 | Atanasov et al. |
| 7,597,936 | B2 | 10/2009 | Smith et al. |
| 2001/0039072 | A1 | 11/2001 | Nagasawa et al. |
| 2002/0064781 | A1 | 5/2002 | Lyles |
| 2002/0068295 | A1 | 6/2002 | Madou et al. |
| 2002/0182627 | A1 | 12/2002 | Wang et al. |
| 2003/0013130 | A1 | 1/2003 | Charych et al. |
| 2003/0215881 | A1 | 11/2003 | Bayley et al. |
| 2003/0232340 | A1 | 12/2003 | Anderson |
| 2004/0033496 | A1 | 2/2004 | Yu et al. |
| 2004/0038260 | A1* | 2/2004 | Martin et al. ............ 435/6 |
| 2004/0048067 | A1 | 3/2004 | O'Gara |
| 2004/0063126 | A1 | 4/2004 | Barton et al. |
| 2004/0067503 | A1 | 4/2004 | Tan et al. |
| 2004/0070309 | A1 | 4/2004 | Nomura et al. |
| 2004/0076681 | A1 | 4/2004 | Dennis et al. |
| 2004/0115680 | A1 | 6/2004 | Garey et al. |
| 2004/0152129 | A1 | 8/2004 | Garey et al. |
| 2004/0183176 | A1 | 9/2004 | Naya et al. |
| 2004/0224321 | A1 | 11/2004 | Nicolau et al. |
| 2004/0253624 | A1 | 12/2004 | Smith et al. |
| 2005/0003521 | A1 | 1/2005 | O'Connor et al. |
| 2005/0019784 | A1 | 1/2005 | Su et al. |
| 2005/0043894 | A1 | 2/2005 | Fernandez |
| 2005/0065028 | A1 | 3/2005 | Pellin et al. |
| 2005/0084865 | A1 | 4/2005 | Yu et al. |
| 2005/0095627 | A1* | 5/2005 | Kolman et al. ............ 435/6 |
| 2005/0130174 | A1 | 6/2005 | Bao et al. |
| 2005/0136408 | A1 | 6/2005 | Tom-Moy et al. |
| 2005/0136463 | A1 | 6/2005 | Kim et al. |
| 2005/0173341 | A1* | 8/2005 | Salinaro ............ 210/636 |
| 2005/0186629 | A1 | 8/2005 | Barth |
| 2005/0191616 | A1 | 9/2005 | Shenoy et al. |
| 2006/0003458 | A1 | 1/2006 | Golovchenko et al. |
| 2006/0019247 | A1 | 1/2006 | Su et al. |
| 2006/0051765 | A1 | 3/2006 | Zhang et al. |
| 2006/0057585 | A1 | 3/2006 | McAllister |
| 2006/0105373 | A1 | 5/2006 | Pourmand et al. |
| 2006/0105461 | A1 | 5/2006 | Tom-Moy et al. |
| 2006/0134397 | A1 | 6/2006 | Smith |
| 2006/0134717 | A1 | 6/2006 | Tellier et al. |
| 2006/0141486 | A1 | 6/2006 | Coonan et al. |
| 2006/0231419 | A1 | 10/2006 | Barth et al. |
| 2007/0132043 | A1 | 6/2007 | Bradley et al. |
| 2007/0298511 | A1 | 12/2007 | Kang et al. |
| 2008/0302660 | A1 | 12/2008 | Kahn et al. |
| 2009/0093011 | A1 | 4/2009 | Fang et al. |
| 2009/0099786 | A1 | 4/2009 | Oliver et al. |
| 2009/0136958 | A1 | 5/2009 | Gershow et al. |

FOREIGN PATENT DOCUMENTS

| | | | |
|---|---|---|---|
| WO | WO 2005/033685 | A2 | 4/2005 |
| WO | WO 2008/030582 | A1 | 3/2008 |
| WO | WO 2008/039579 | A2 | 4/2008 |

OTHER PUBLICATIONS

Vlassiouk et al (Langmuir, vol. 20, Supporting Information, published on the web Dec. 14, 2004).*

Bailey, Ryan C. et al., "Real-Time Multicolor DNA Detection with Chemoresponsive Diffraction Gratings and Nanoparticle Probes", J. Amer Chem Soc., vol. 125 2003, 13541-13547.

Brockman, Jennifer M. et al., "Surface Plasmon Resonance Imaging Measurements of Ultrathin Organic Films", Annu. Rev. Phys. Chem, vol. 51 2000, 41-63.

Cao, Yunwei C. et al., "Nanoparticles with Raman Spectroscopic Fingerprints for DNA and RNA Detection", Science, vol. 297 Aug. 30, 2002, 1536-1540.

Chang, H. et al., "DNA-Mediated Fluctuations in Ionic Current Through Silicon Oxide Nanopore Channels", Amer Chem Soc., Nano Letters, vol. 4, No. 8 Jul. 7, 2004, 1551-1556.

Chen, Peng et al., "Atomic Layer Deposition to Fine-Tune the Surface Properties and Diameters of Fabricated Nanopores", Amer Chem Soc. Nano Letters, vol. 4, No. 7 Jun. 25, 2004, 1333-1337.

Cui, X. D. et al., "Making electrical contacts to molecular monolayers", Nanotechnology vol. 13, Institute of Physics Publishing 2002, 5-14.

Cui, X. D. et al., "Reproducible Measurement of Single-Molecult Conductivity", Science vol. 294 Oct. 19, 2001, 571-574.

Deamer, David W. et al., "Characterization of Nucleic Acids by Nanopore Analysis", Amer Chem Society, Accounts of Chemical Research, vol. 35, No. 10 Sep. 27, 2002, 817-825.

Demers, Linette M. et al., "A Fluorescence-Based Method for Determining the Surface Coverage and Hybridization Efficiency of Thiol-Capped Oligonucleotides Bound to Gold Thin Films and Nanoparticles", Analytical Chemistry vol. 72, American Chemical Society Nov. 15, 2000, 5535-5541.

Dunbar, T. D. et al., "Combined Scanning Tunneling Microscopy and Infrared Spectroscopic Characterization of Mixed Surface Assemblies of Linear Conjugated Guest Molecules in Host Alkanethiolate Monolayers on Gold", J. Phys. Chem. B vol. 104, American Chemical Society 2000, 4880-4893.

Fodor, Stephen P. et al., "Multiplexed Biochemical Assays with Biological Chips", Nature Product Review, vol. 364 Aug. 5, 1993, 555-556.

Gyurcsanyi, Robert E. et al., "Biorecognition-Modulated Ion Fluxes Through Functionalized Gold Nanotubules as a Novel Label-Free Biosensing Approach", J of Royal Society of Chemistry 2003, 2560-2561.

Hartwich, Gerhard et al., "Electrochemical Study of Electron Transport through Thin DNA Films", J. Am. Chem. Soc. vol. 121, American Chemical Society 1999, 10803-10812.

Herne, Tonya M. et al., "Characterization of DNA Probes Immobilized on Gold Surfaces", J. Am. Chem. Soc. vol. 119, American Chemical Society 1997, 8916-8920.

Jessensky, O. et al., "Self-organized formation of hexagonal pore arrays in anodic alumina", Applied Physics Letters vol. 72, No. 10, American Institute of Physics Mar. 9, 1998, 1173-1175.

Kang, Myungchan et al., "Protein Capture in Silica Nanotube Membrane 3-D Microwell Arrays", Analytical Chemistry vol. 77, No. 19, American Chemical Society Oct. 1, 2005, 7243-6249.

Kohli, Punit et al., "DNA-Functionalized Nanotube Membranes with Single-Base Mismatch Selectivity", Science, vol. 305 Aug. 13, 2004, 984-986.

Kohli, Punit et al., "Nanotube Membrane Based Biosensors", Electroanalsis, vol. 16, No. 1-2 2004.

(56) References Cited

OTHER PUBLICATIONS

Krasnoslobodtsev, Alexey V. et al., "Effect of Water on Silanization of Silica by Trimethoxysilanes", *Langmuir* vol. 18, American Chemical Society 2002, 3181-3184.

Krasnoslobodtsev, Alexey et al., "Surface Assisted Intermolecular Interactions in Self-Assembled Coumarin Submonolayers", *Langmuir* vol. 17, American Chemical Society 2001, 7593-7599.

Leatherman, G. et al., "Carotene as a Molecular Wire: Conducting Atomic Force Microscopy", *J. Phys. Chem. B* vol. 103, American Chemical Society 1999, 4006-4010.

Lee, Sang B. et al., "Electromodulated Molecular Transport in Gold-Nanotube Membranes", *J. Am. Chem. Soc.* vol. 124, American Chemical Society 2002, 11850-11851.

Lee, Sang B. et al., "pH-Switchable, Ion-Permselective Gold Nanotubule Membrane Based on Chemisorbed Cysteine", *Analytical Chemistry* vol. 73, No. 4, American Chemical Society Feb. 15, 2001, 768-775.

Li, An-Ping et al., "Fabrication and Microstructuring of Hexagonally Ordered Two-Dimensional Nanopore Arrays in Anodic Alumina", *Advanced Materials* vol. 11, No. 6, Wiley-VCH Verlag GmbH, Weinheim 1999, 483-487.

Li, A. P. et al., "Hexagonal pore arrays with a 50-420 nm interpore distance formed by self-organization in anodic alumina", *Journal of Applied Physics* vol. 84, No. 11, American Institute of Physics Dec. 2, 1998, 6023-6026.

Liquier, Jean et al., "Infrared Spectroscopy of Nucleic Acids", *Infrared Spectroscopy of Biomolecules, Mantsch, Henry H., et al. ed.* Wiley-Liss, Inc., New York, New York 1996, 131-158.

Macbeath, Gavin et al., "Printing Proteins as Microarrays for High-Throughput Function Determination", *Science* vol. 289 Sep. 8, 2000, 1760-1763.

Martin, Charles R. et al., "Controlling Ion-Transport Selectivity in Gold Nanotubule Membranes", *Advanced Materials* vol. 13, No. 18, Verglag GmbH, D-79469 Weinheim Sep. 14, 2001, 1351-1362.

Matsumoto, Futoshi et al., "Flow-Through-Type DNA Array Based on Ideally Ordered Anodic Porous Alumina Substrate", *Advanced Materials* vol. 16, No. 23-24, Wiley-VCH Verlag GmbH & Co., KGaA, Weinheim Dec. 17, 2004, 2105-2108.

Matsumoto, Futoshi et al., "Ideally Ordered, High-Density Patterning of SNA on Au Disk Array Fabricated Using Anodic Porous Alumina", *Japanese Journal of Applied Physics* Vo. 43, No. 5A, The Japan Society of Applied Physics 2004, L640-L643.

Miney, Paul G. et al., "Growth and Characterization of a Porous Aluminum Oxide Film Formed on an Electrically Insulating Support", *Electrochemical and Solid-State Letters* vol. 6, No. 10, The Electrochemical Society, Inc. 2003, B42-B45.

Muller, F. et al., "STructuring of Macroporous Silicon for Applications as Photonic Crystals", *Journal of Porous Materials* vol. 7, Kluwer Academic Publishers, The Netherlands 2000, 201-204.

Nakane, Jonathan J. et al., "Nanopore sensors for nucleic acid analysis", *Journal of Physics: Condensed Matter* vol. 15, Institute of Physics Publishing 2003, R1365-R1393.

Neish, Calum S. et al., "Direct visualization of ligand-protein interactions using atomic force microscopy", *British Journal of Pharmacology* vol. 135, Nature Publishing Group 2002, 1943-1950.

Nitsche, Johannes M.. et al., "Hindered Brownian Diffusion of Spherical Solutes within Circulat Cylindrical Pores", *Ind. Eng. Chem. Res.* vol. 33, American Chemical Society 1994, 2242-2247.

Noy, Aleksandr et al., "Stretching and breaking duplex DNA by chemical force microscopy", *Chemistry & Biology* vol. 4, No. 7 1997, 519-527.

Pan, Shanlin et al., "Interferometric Sensing of Biomolecular Binding Using Nanoporous Aluminum Oxide Templates", *Amer Chem Soc Nano Letters*, vol. 3, No. 6 Apr. 24, 2003, 811-814.

Rawlett, Adam M. et al., "Electrial measurements of a dithiolated electronic molecule via conducting atomic force microscopy", *Applied Physics Letter* vol. 81, No. 16, American Institute of Physic Oct. 14, 2002, 3043-3045.

Roth, Kristian M. et al., "Measurements of Electron-Transfer Rates of Charge-Storage Molecular Monolayers on Si(100). Toward Hybrid Molecular/Semiconductor Information Storage Devices", *J. Am. Chem. Soc.* vol. 125, American Chemical Society 2003, 505-517.

Satjapipat, Munlika et al., "Selective Desorption of Alkanethiols in Mixed Self-Assembled Monolayers for Subsequent Oligonucleotide Attachment and DNA Hybridization", *Langmuir* vol. 17 2001, 7637-7644.

Schena, Mark et al., "Quantitative Monitoring of Gene Expression Patterns with a Complementary DNA Microarray", *Science* vol. 270 Oct. 20, 1995, 467-470.

Sosnowski, Ronald G. et al., "Rapid determination of single base mismatch mutations in DNA hybrids by direct electric field control", *Proc. Natl. Acad. Sci. USA* vol. 94 Feb. 1997, 1119-1123.

Southern, E. M., "Detection of Specific Sequences Among DNA Fragments Separated by Gel Electrophoresis", *J. Mo. Biol.* 1975, 503-517.

Szczepanski, Victor et al., "Stability of silane modifiers on alumina nanoporous membranes", *Journal of Membrance Science* vol. 281, Elsevier B.V. Apr. 28, 2006, 587-591.

Takmakov, Pavel et al., "Application of anodized aluminum in fluorescence detection of biological species", *Anal. Bioanal. Chem.* vol. 385 May 25, 2006, 954-958.

Taton, T. A. et al., "Scanometric DNA Array Detection with Nanoparticle Probes", *Science* vol. 289 Sep. 8, 2000, 1757-1760.

Taton, T. A. et al., "The DNA-Mediated Formation of Supramolecular Mono-and Multilayered Nanoparticle Structures", *J. Am. Chem. Soc.* vol. 122, American Chemical Society 2000, 6305-6306.

Van Beuningen, Rinie et al., "Fast and Specific Hybridization Using Flow-Through Microarrays on Porous Metal Oxide", *Clinical Chemistry* Vo. 47, No. 10 2001, 1931-1933.

Vlassiouk, Ivan et al., "Direct" Detection and Separation of DNA Using Nanoporous Alumina Filters, *Langmuir* vol. 20, American Chemical Society Oct. 14, 2004, 9913-9915.

Vlassiouk, Ivan et al., "Sensing DNA Hybridization via Ionic Conductance through a Nanoporous Electrode", *Langmuir* vol. 21, American Chemical Society 2005, 4776-4778.

Wirtz, Marc et al., "Template-Synthesized Nanotubes for Chemical Separations and Analysis", *Chem. Eur. J.* vol. 8, No. 16, Wiley-VCH Verlag GmbH & Co., KAaA, Weinheim 2002, 3572-3578.

Wu, Ying et al., "Quantitative assessment of a novel flow-through porous microarray for the rapid analysis of gene expression profiles", *Nucleic Acids Research* vol. 32, No. 15, Oxford University Press Aug. 27, 2004, 1-7.

Zhu, Heng et al., "Global Analysis of Protein Activities Using Proteome Chips", *Science* vol. 293 Sep. 14, 2001, 2101-2105.

Vlassiouk, Ivan et al., "Ionic Selectivity of Single Nanochannesl", Nano Letters, vol. 8, No. 7, American Chemical Society, 2008, 1978-1985.

* cited by examiner

US 8,906,609 B1

LABEL-FREE BIOMOLECULE SENSOR BASED ON SURFACE CHARGE MODULATED IONIC CONDUCTANCE

CROSS-REFERENCE TO RELATED APPLICATIONS

This application claims priority to and the benefit of U.S. Provisional Patent Application No. 61/237,926, titled "Label-Free Biomolecule Sensor Based on Surface Charge Modulated Ionic Conductance", filed Aug. 28, 2009. This application is a Continuation-In-Part application of U.S. patent application Ser. No. 11/948,187, titled "Sensing Hybridization Through A Nanoporous Electrode", filed Nov. 30, 2007, which claims the benefit of the filing of U.S. Provisional Patent Application Ser. No. 60/720,790, titled "Sensing DNA Hybridization Via Ionic Conductance Through a Nanoporous Electrode", filed Sep. 26, 2005, and which is a Continuation-In-Part application of U.S. patent application Ser. No. 11/527,845, titled "Sensing Hybridization Via Ionic Conductance Through a Nanoporous Electrode, filed Sep. 26, 2006, which claims the benefit of the filing of U.S. Provisional Patent Application Ser. No. 60/720,790, titled "Sensing DNA Hybridization Via Ionic Conductance Through a Nanoporous Electrode", filed Sep. 26, 2005. This application is also related to U.S. patent application Ser. No. 11/763,241, titled "Detection of a Biological Target Using Nanopores", filed Jun. 14, 2007. The specification and claims of all applications and patents referenced herein are incorporated by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. S06 GM 08136-26 awarded by the U.S. NIH and grant GM08136 awarded by U.S. NIH (SCORE).

REFERENCE TO SEQUENCE LISTING

This application contains a DNA sequence listing, and the sequence listing is contained in an electronic file named "37000-0906_NMSU-Smirnov5_ST25.txt" created on Mar. 12, 2010, submitted with this application. The file size is 2 kilobytes. The contents of the file submitted with this application are hereby incorporated by reference into the specification.

BACKGROUND OF THE INVENTION

1. Field of the Invention (Technical Field)

Embodiments of the present invention relates to the use of membrane substrates having nano-sized pores within which capturing elements of a biological or chemical nature are immobilized for the detection of target biological objects, or analytes, using changes in ionic conductance through the nanopores as a result of hybridization between the capturing elements and the target biological objects. The present invention also relates to the use of membranes having nano-sized pores in which complimentary ligands are immobilized for the detection of complimentary target analytes through hybridization wherein detection utilizing changes in ionic conductance through the nanopores as a result of surface charge change from hybridization.

2. Background Art

DNA microarray chips for the detection of oligonucleotides, as known in the art, rely on such detection means as the fluorescence detection of modified DNA oligonucleotides. Controlling the mass transport of specific species through nanopores by means of UV light, pH of solution, charge, and size of an ion has been explored. Biosensors and separation membranes that are based on selective nanopores have been studied, and technological advances have made it possible to manufacture nanopores with dimensions comparable to the sizes of biological polymers such as short DNA and peptides. Advantage has been made of such an approach and single nanopores have been used to resolve the sequences of individual DNA molecules linked to a degree of partial pore blockage by the DNA.

Detection and separation of DNA using nanoporous alumina filters has also been accomplished. U.S. patent application Ser. No. 11/235,824 filed Sep. 26, 2005 disclosed detection and separation apparatuses and methods. U.S. patent application Ser. No. 11/235,824 is incorporated herein by reference.

Alternative electrical detection schemes usually involve electrochemical methods that also require complicated detection means and methods. Measuring changes in ionic conductance through a nanopore or a nanoporous membrane presents an opportunity to more easily detect target biological objects.

Applications of nanotechnology are particularly versatile when it comes to chemical and biochemical sensors. Bioaffinity interactions such as DNA-DNA and antigen-antibody are typically employed for identification of the presence of a particular DNA sequence in a sample, for detection of microbial and viral species. The mechanism of detecting such an interaction with untagged biochemical analytes can vary broadly and utilize the change of mass, volume, charge, optical, or other properties of the analytes.

Because of a large surface/volume ratio in nanoporous materials, the ionic conductance through the pores is greatly affected by the ions' interaction with the walls. This interaction can manifest itself through different mechanisms, most commonly via the "volume exclusion" and the "surface charge" mechanisms. Previously, we have demonstrated the utilization of the volume exclusion mechanism for DNA detecting. In this mechanism, small diameter pores get "clogged" as a result of binding targeted DNA onto single-stranded DNA (ss-DNA) covalently attached to the walls. The result is detected by a drop in ionic flux through the pores. The observed effect was strongly dependent on the pore diameter: almost nonexistent with 200 nm pores and reaching in excess of 50% in 20 nm or smaller pores.

Note that where the discussion herein refers to a number of publications by author(s) and year of publication, that, due to recent publication dates, certain publications are not to be considered as prior art vis-à-vis the present invention. Discussion of such publications herein is given for more complete background and is not to be construed as an admission that such publications are prior art for patentability determination purposes.

BRIEF SUMMARY OF THE INVENTION

Embodiments of the present invention comprise a method for the detection of a biological analyte (including but not limited to oligonucleotides) using ionic conductance through a nanoporous membrane that is altered when a biological analyte (e.g., an oligonucleotide or an antigen) hybridizes with a complementary biological analyte (or "capturing element") immobilized on a modified membrane filter.

Thus, an embodiment of the present invention provides a method for detecting a variation of ionic conductivity in nano-sized pores ("nanopores"), the method comprising providing a membrane substrate having nano-sized pores, covalently binding a capturing element that is complementary to a target biological object onto the membrane substrate, exposing the target biological object to the membrane substrate so that the target biological object binds to the capturing element, and detecting a variation of ionic conductivity in the membrane substrate upon hybridization of the capturing element to the target biological object. The capturing element may comprise DNA, RNA, morpholino, PNA, or other nucleic acid analogs, an enzyme, a virus, an antigen, an antibody, or a combination of these. The target biological object may be a nucleic acid (e.g., DNA or RNA), an enzyme, a virus, an antigen, an antibody, or a combination of these. The membrane substrate may be an anodized aluminum oxide filter substrate. The anodized oxide filter substrate may be hydrothermally treated prior to binding the capturing element onto the substrate. At least a portion of the nano-sized pore comprises a diameter of approximately 200 nm or less.

Another embodiment of the present invention provides an apparatus for detection of a target biological object, the apparatus comprising a membrane substrate having nano-sized pores ("nanopores"), a capturing element covalently bound onto the walls of the pores, wherein the capturing element is complementary to a target biological object, two electrodes located on each side of the nano-sized pores. In still another embodiment, a three electrode scheme is utilized having a working electrode on one side and a counter and a reference electrode on the opposite side of the nano-sized pores. The membrane substrate may be an anodized aluminum oxide filter substrate with pore diameters less than 200 nm and its surface functionalized using silane chemistry. The nano-sized pores may be additionally narrowed by hydrothermal treatment before functionalization.

Embodiments of the present invention provide a simple, efficient method for the detection of biological objects that requires no modification of target species and can be used to detect various biochemical species simultaneously.

One embodiment of the present invention comprises a method for detecting biological analytes comprising a nucleic acid sequence with a charged backbone using ionic conductance through one or more nano-sized pores. This embodiment preferably comprises providing a nanoporous membrane substrate having one or more nano-sized pores, covalently binding onto a wall of the one or more nano-sized pores a capturing element comprising a morpholino sequence and/or a peptide nucleic acid (PNA) sequence, wherein the morpholino and/or PNA sequence comprises a neutral charged backbone structure. This embodiment also preferably comprises exposing the capturing element that is covalently bound onto the wall of the one or more nano-sized pores to a solution possessing the biological analytes so that the biological analytes specifically bind to the capturing element and alters the surface charge of the nanopore, and detecting an increase of ionic conductance through the one or more nano-sized pores upon specific binding of the capturing element and the biological analyte. In this embodiment, the biological analytes may be a second nucleic acid (e.g., DNA or RNA) wherein the first nucleic acid sequence and the second nucleic acid sequence are the same or different, an enzyme, a virus, an antigen, an antibody, or a combination of these. The membrane substrate may have an oxide surface. The one or more nano-sized pores may be narrowed by physical or chemical treatment of the materials. At least a portion of the nano-sized pore comprises a diameter of approximately 200 nm or less.

Another embodiment of the present invention comprises an apparatus for detection of a biological analyte. The apparatus preferably comprises a membrane substrate having nano-sized pores and a morpholino sequence and/or a PNA sequence, wherein the morpholino and/or PNA sequence comprises a neutral charged backbone structure, covalently bound onto a wall of the nano-sized pores, and wherein the morpholino and/or PNA sequence is complementary to said biological analyte. In this embodiment, the membrane substrate may comprise an anodized aluminum oxide filter substrate and may be functionalized with aminosilane and glutaraldehyde. The anodize oxide substrate can also be hydrothermally treated substrate. At least a portion of the plurality of nano-sized pores can comprise a diameter of approximately 200 nm or less.

Objects, advantages and novel features, and further scope of applicability of the present invention are set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention.

DETAILED DESCRIPTION OF THE INVENTION

Figure 1:
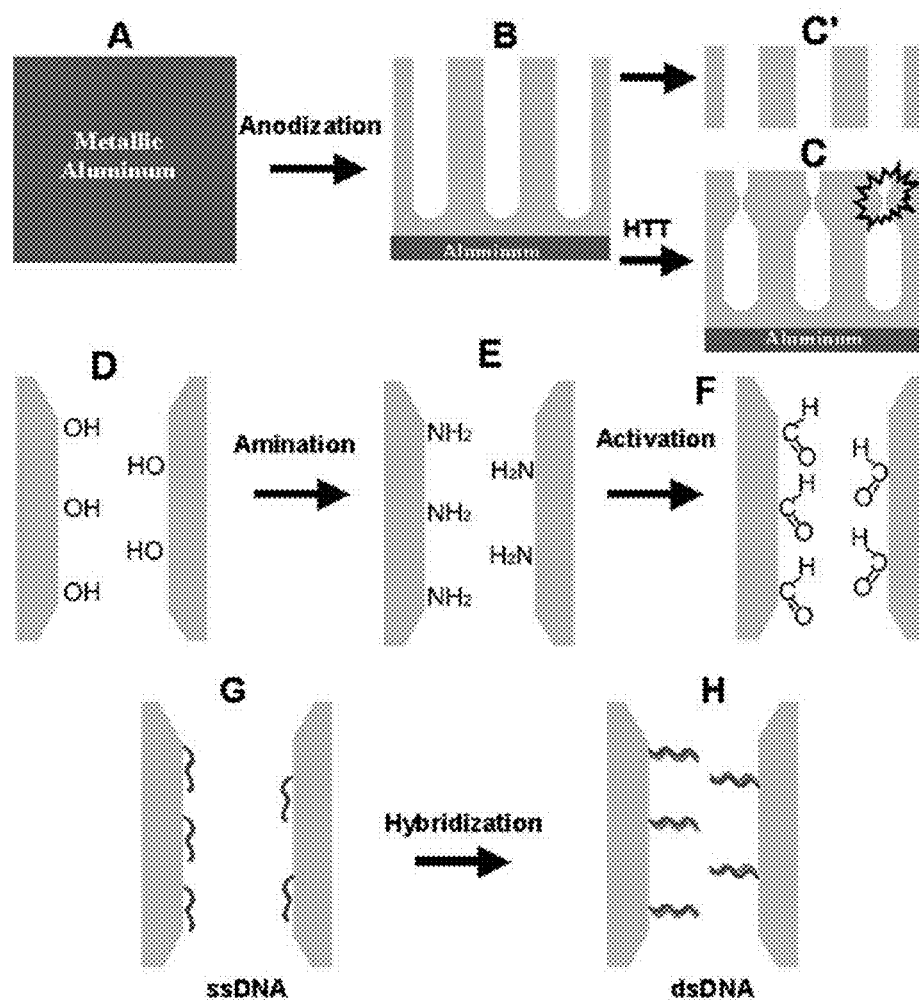
FIG. 1 shows a schematic of an embodiment of the present invention demonstrating the anodization and preparation of an aluminum oxide membrane to form nanopores, which can either be freed as a membrane (C') or altered to further narrow pores (C), e.g., by hydrothermal treatment, the immobilization of a ssDNA in the nanopores, and its hybridization with a target DNA.

An embodiment of the present invention provides for the use of membrane substrates having nano-sized pores modified with capturing elements for detecting single stranded oligonucleotides such as nucleic acids, enzymes, viruses, antigens, antibodies, and other species (i.e., the present invention can be used with biological objects that possess bioaffinity interactions) using change in ionic conductance through nanopores resulting from the binding of analytes to their complementary capturing elements (nucleic acids, antibodies, etc.) covalently attached on the wall surfaces of the membrane. The analytes require no modification, and different species can be simultaneously measured on a single substrate. Reference is made to Vlassiouk, Ivan, et al., "Sensing DNA Hybridization via Ionic Conductance Through a Nanoporous Electrode", *Langmuir*, 21 (2005) 4776-4778 and to Takmakov, Pavel, et al., "Hydrothermally Shrunk Alumina Nanopores and their Application to DNA Sensing", *Analyst*, 131 (2006) 1248-1253, and those references are incorporated herein by reference.

As used herein, the words "a", "an", and "the" mean one or more, and the words "substrate" and "membrane" mean any material that can serve as a support structure capable of defining nanopores. "Nanopore" is defined as a pore that comprises a cross section with dimensions of less than 200 nm, and "nano-sized" means comprising such a cross sectional area. The terms "nanopore" and "nano-sized pores" are used interchangeably herein. The scope of the present invention includes pores that are "nano-sized", preferably less than 200 nanometers in cross section. It is understood that the size of the nanopore is preferably a size that allows for effective immobilization of complementary oligonucleotides such that target oligonucleotides are effectively and efficiently bound to the complimentary oligonucleotides (and/or other complimentary and target biological objects) and such that the detection or measurement of changes in ionic conductance is facilitated.

Although the scope of the present invention includes oligonucleotides and other biological objects that possess bioaffinity interactions, DNA is discussed herein in detail for illustrative purposes as one embodiment that is representative of the present invention. Also, the scope of the present invention includes the use of any substrate material known in the art that can be functionalized, or otherwise used, to immobilize oligonucleotides and/or other biological objects of interest that possess bioaffinity interactions.

Ionic conductance through nanoporous channels is a practical tool for fast, inexpensive, and convenient detection of chemical and biological species. This method of detection has several advantages over the existing techniques such as microarrays, including the employment of a convenient electrical detection and no need for labeling the analyte molecules.

Conductance variation through the pores caused by changes resulting from analyte binding allows for parallel detection of a number of analytes on a single microarray chip, where recognition would rely on specificity of the binding of the analyte to differently modified spots of the array, similar to standard fluorescent microarrays.

The ionic conductance through nanopores can alter as a result of analyte binding either as a result of the volume exclusion effect or as a result of a change in surface charge. In the former situation, the current through the nanopores reduces when analyte binds to the nanopore walls and thus decreases the effective cross section of the channel. The charge effect is observed when the low ion concentration becomes less than the concentration of counter-ions in the channel that neutralize charge on the walls. Binding of charged analytes to the channel walls in this situation affects the ion concentration in the pore and thus the resulting conductance.

A non-limiting example of a substrate or membrane that can be utilized for the formation of nanopores is that of anodized alumina membranes. Hydroxyl groups on the alumina surface can be used for chemical functionalization. Alumina nanoporous membranes provide a convenient substrate for high density immobilization of aminated DNA via covalent linking using aminosilane and glutaraldehyde. The high surface density of DNA (greater than approximately $4 \times 10^{12}$ $cm^{-2}$) and high efficiency of hybridization (greater than approximately 70%) in combination with high surface area provide for convenient detection methods of nucleic acid. The modified nanopores described herein can be used to detect DNA binding using a change in ionic conductivity that is measurable via, for example, redox pairs or electrolyte. Thus, nanoporous alumina membrane modified with covalently bound nucleic acid can be used to detect target DNA by monitoring the ionic impedance change upon DNA hybridization. Immobilization onto the membrane may be accomplished by any means known in the art, such as, but not limited to, the method described herein wherein covalent bonding is utilized.

In a non-limiting embodiment of the present invention, immobilization is performed in several steps such as silanization with aminosilane, activation with glutaraldehyde, and covalent attachment of an aminated DNA oligomer or an aminated nucleic acid analog. The glutaraldehyde linker is utilized to join the amino groups of aminated DNA and the terminal amino group of aminosilane to achieve covalent binding of DNA inside the nanopores. Unreacted glutaraldehyde may be neutralized by proplylamine.

Thus, in a non-limiting example as shown in FIG. 1, the immobilization of DNA onto a membrane substrate is performed as follows. The membrane is prepared by anodizing aluminum foil (A to B). It is either released as a free standing membrane by dissolving aluminum (in $CuCl_2$) and opening pore endings in phosphoric acid (B to C'). Alternatively, the membrane is left on aluminum and the pores are narrowed by boiling (hydrothermal treatment) in water (B to C). The boiling takes place for a suitable period of time, up to approximately 1 hour.

DNA immobilization on the activated surface follows (as described in Vassiouk, I., et al., "'Direct' Detection and Separation of DNA Using Nanoporous Alumina Filters", *Langmuir*, 20, (2004), 9913; Takmakov, Pavel, et al., "Hydrothermally Shrunk Alumina Nanopores and their Application to DNA Sensing", *Analyst*, 131 (2006) 1248-1253; Szczepanski, V., et al., "Stability of Silane Modifiers on Alumina Nanoporous Membranes", *J. Membr. Sci*, 281, (2006), 587; and Takmakov, P., et al., "Application of Anodized Aluminum in Fluorescence Detection of Biological Species", *Anal. Bioanal. Chem.*, 385, (2006), 954, and those references are incorporated herein by reference. The membrane is immersed into a 5% acetone solution of 3-amino-propyltrimethoxysilane for approximately 1 hour so that the aminopropyl-trimethoxysilane reacts with OH surface groups resulting in amino groups (D to E). The membrane is then washed thoroughly with acetone or toluene and baked at approximately 120° C. for approximately 20-30 minutes. The membrane is left overnight in an 8% aqueous solution of glutaraldehyde so that the amino groups react with the glutaraldehyde (E to F). The membrane is then washed with water and dried.

In this example, approximately 30 μL of an aqueous solution of 5'-aminated ssDNA (1 mM) is placed onto the membrane wherein it reacts with surface aldehydes (F to G) and kept at high humidity overnight. The membrane is then thoroughly washed by passing a 1.0 M NaCl solution through it. Preferably, for improving selectivity of hybridization, unreacted glutaraldehyde on the surface is neutralized by exposing it overnight to a $10^{-5}$ M aqueous solution of propylamine.

Hybridization with a complementary ss-DNA (G to H) is performed in a 1.0 M NaCl solution at room temperature for approximately 1 hour. To minimize false readings, the membrane after hybridization is preferably thoroughly washed with 1.0 M NaCl solution.

Electrical detection is desirable because of simplicity and easy interfacing. It is also convenient for miniaturization, integration into existing detection schemes, and realization in the form of parallel arrays.

Thus, as a non-limiting example, cyclic voltammetry (CV), time dependence of direct current (dc), and impedance spectroscopy with $Fe(CN)_6^{4-/3-}$ and $Ru(NH_3)_6^{2+/13+}$ redox pairs can be used to probe the efficiency of ion blockage. Such redox pairs are chosen because of their relatively large size, reversible electrochemistry, and differing charges.

Anodized alumina membranes with 20-nm diameter pores across a portion of L=60 μm thickness were oriented by the narrow pores towards the working electrode. The pores on the small diameter side are comparable to the DNA length, nearly 7.5 nm for a double-stranded 21-mer, and thus are expected to affect the conductance the most.

The ionic conductance through nanopores changes as a result of: (a) volume exclusion due to additional DNA upon hybridization, (b) the ionic mobility change inside the pores entangled with charged DNA strings. The complexity is revealed in the initial decrease of impedance after immobilization of ss-DNA inside the nanopores, as compared to an unmodified filter. In contrast, the impedance always increases (amplitude of CV decreases) upon hybridization of already immobilized DNA with the complementary oligomer.

Thus, nanoporous alumina with covalently linked ss-DNA on its surface can be used for electrical detection of complementary target DNA sequences without a need for their modification. Electrical detection offers a greater versatility in miniaturization, integration into inexpensive detection schemes, and realization of parallel arrays, that is, DNA chips. The theoretical sensitivity limit for this geometry can be conservatively estimated using experimental data by taking electrodes of 5 μm×5 μm area and 0.5-μm-thick oxide pores of 20-nm diameter. In that situation, less than $10^{-17}$ mol of complementary target DNA is required to hybridize surface-immobilized ss-DNA with the same density, $10^{12}$ cm$^{-2}$, as in the described cell. More than a 70% impedance increase results.

Figure 2:
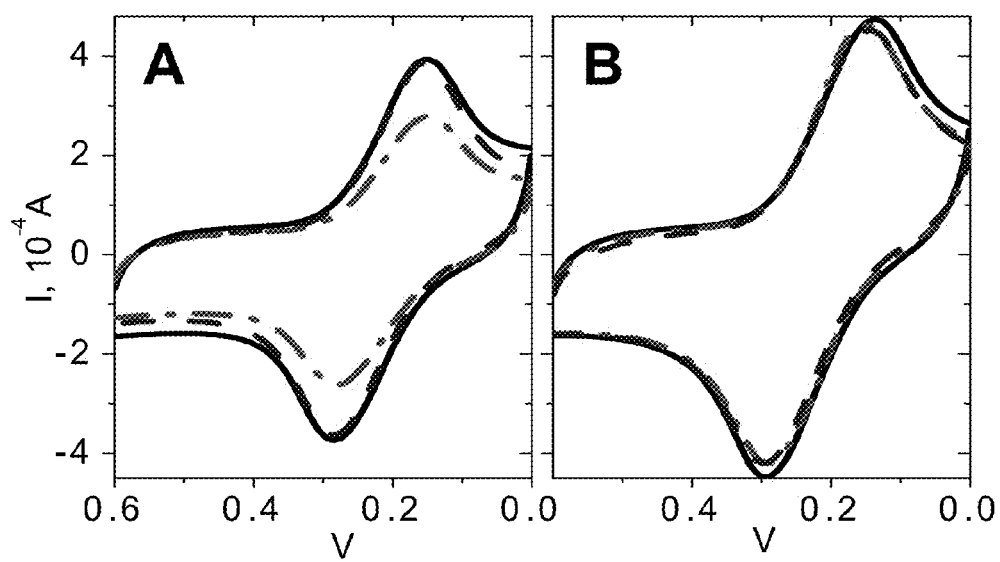
FIG. 2 shows cyclic voltammetry (CV) in the region for $Fe(CN)_6^{3-/4-}$ oxidation/reduction (A) and that for $Ru(NH_3)_6^{2+/3+}$ (B), of the membrane with 20 nm pore size modified with 21-mer ss-DNA immobilized inside the pores.; the signal decreases after hybridization with the complementary 21-mer but recovers after denaturing.
Figure 3:
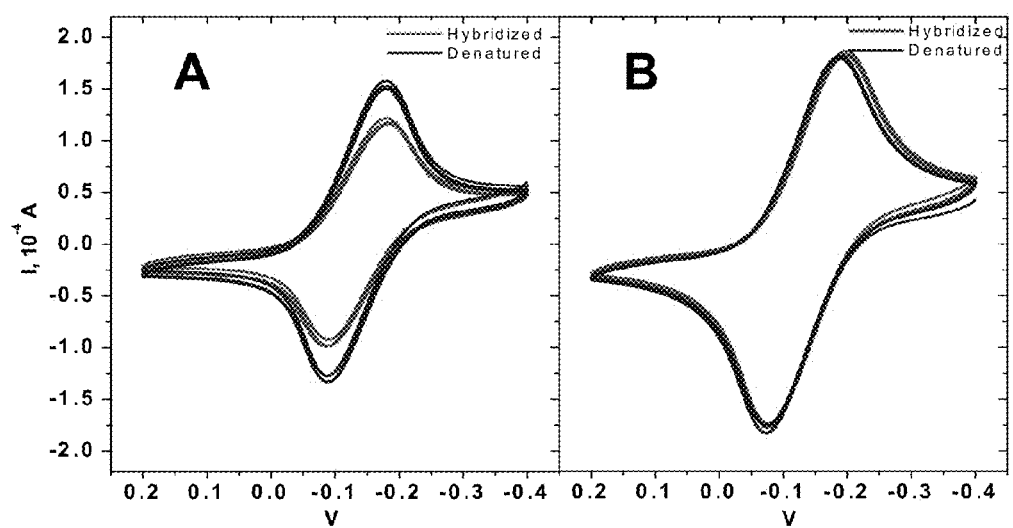
FIG. 3 shows CV in the region for $Ru(NH_3)_6^{2+/3+}$ oxidation/reduction, the conditions of FIG. 2.

FIGS. 2 and 3 illustrate a non-limiting example for electrical detection using cyclic voltammetry. A flat platinum working electrode is placed in close contact with the tested side of a membrane, while a screen counter electrode is in contact with the opposite side. Such geometry minimizes contribution from the solution outside the membrane, which is mostly distinguishable at high frequencies. The detection is more convenient when the membrane is oriented to the working electrode by the side with smaller pore diameter.

As previously noted, anodized alumina membranes can be hydrothermally treated (e.g., by boiling). Doing so shrinks their diameters. For example, with respect to pores of approximately 60 nm diameters grown from anodization in oxalic acid at 40 V, the pores shrink to a neck of less than 10 nm in diameter and 2-4 μm in length, in which the diffusion coefficient of ions is five orders of magnitude smaller than in the bulk. DNA sensing wherein a target DNA is hybridized with a complementary ssDNA covalently immobilized inside the nanopores, results in an increase in impedance by more than 50% whereas a non-complementary ssDNA has no measurable effect.

Hydrothermally treated alumina membranes have high resistance and thus allow ionic conductance detection without the noble metal electrodes and oxidation/reduction of electro-active species.

Because, following hydrothermal treatment, the pore resistance exceeds that of the electrolyte, nanopores in a microarray format can be utilized. Patterned arrays of aluminum electrodes can be individually anodized and uniquely modified with different DNA or other biomolecules. These electrodes can be independently addressed against a common counter electrode.

INDUSTRIAL APPLICABILITY

The invention is further illustrated by the following non-limiting examples. All procedures and measurements were done at 25° C. unless mentioned otherwise.

Example 1

1. DNA Sequences:

The DNA sequences used in this example were as follow: Surface bound 21-mer: 5'NH$_2$-GCT TAG GAT CAT CGA GGT CCA, $\epsilon_1$(260 nm)=2.25×10$^5$ M$^{-1}$ cm$^{-1}$ (SEQ ID NO:1); Complement 21-mer: 5'-TGG ACC TCG ATG ATC CTA AGC, $\epsilon_3$(260 nm)=2.25×10$^5$M$^{-1}$ cm$^{-1}$ (SEQ ID NO:2); and Surface bound 21-mer without a complement sequence: 5'NH2-GGC CTT AAT CGG ATA GAG TGA, $\epsilon_4$(260 nm)=2.38×10$^5$ M$^{-1}$ cm$^{-1}$ (SEQ ID NO:3).

2. Electrochemical Measurements:

All electrochemical measurements in this example were performed using 604B electrochemical analyzer (CH Instruments), a flat platinum working electrode, and a reference Ag/AgCl mini-electrode and stainless steel screen counter electrode with modified membrane in close contact with the working electrode. Before each experiment, the working electrode was polished with 0.05µ gamma alumina powder using polishing kit (CH Instruments). Stainless mesh (Fisher) was employed as a counter electrode. Electrochemical measurements were performed using 10 mM solutions of analyte (Fe(CN)$_6^{-3/-4}$ or Ru(NH$_3$)$_6^{2+/3+}$) in 0.1 M KCl. CV rate was 100 mV/s. FIGS. 2 and 3 illustrate the importance of the pore diameter but insignificance of the ion charge on the result—CV in the region of Fe(CN)$_6^{-3/-4}$ (FIG. 3) and Ru(NH$_3$)$_6^{2+/3+}$ (shown in FIG. 4) show the same effect: The membrane is modified with 21-mer ss-DNA immobilized inside pores, and its signal drops upon hybridization with the complementary target 21-mer. An effect is observed with 20 nm pores (A) but is absent with 200 nm pores (B).

FIG. 2 shows cyclic voltammetry (CV) in the region for Fe(CN)$_6^{3-/4-}$ oxidation/reduction at (A) the 20-nm side of a modified membrane and at (B) the 200-nm side. Solid black lines 10 represent the CV for the membrane with 21-mer ss-DNA immobilized inside pores; dashed-dotted line 20 represents the CV when a complementary 21-mer strand is hybridized on the surface; and dashed line 30 represents the effect after denaturing with 9 M urea. The parameters/conditions are: voltage versus Ag/AgCl; 100 mV/s; 10 mM Fe(CN)$_6^{3-}$/10 mM Fe(CN)$_6^{4-}$ in 0.1 M KCl.

Figure 4:
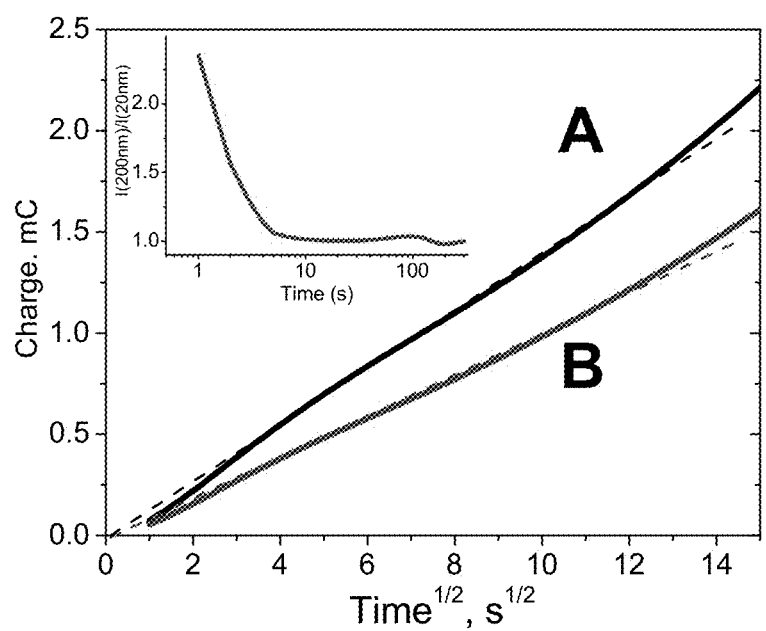
FIG. 4 shows a chronocoulometric plot for a charge passed through the modified nanoporous membrane modified with 21-mer ss-DNA immobilized inside the pore filter before (A) and after (B) hybridization with the complementary 21-mer.

The CV in FIG. 2(A) shows that both reductive and oxidative currents decrease after DNA hybridization occurs inside the nanopores and when the 20-nm side is oriented toward the working electrode, while no noticeable current change was observed with 200-nm pores filter (FIG. 2(B)) because the length of double-stranded DNA (ds-DNA) is much smaller than the pore diameter. The higher current amplitude in 200-nm membrane is a result of a higher ion mobility through larger pores. The CV amplitude did not change in either case side when a non-complementary target DNA was used, in agreement with the lack of hybridization (confirmed by optical measurements). The current amplitude with 20-nm pores recovered to its original value upon DNA denaturing with 9 M urea, while no effect was observed with 200-nm pores. Because of a small Debye length, $\lambda_D$=0.307/c$^{1/2}$, in 0.1 M KCl (~1 nm), no specificity to the ion charge was anticipated. Indeed, similar results were obtained with the positively charged Ru(NH$_3$)$_6^{2+/3+}$ redox pair (FIG. 3). A change in conductivity can also be observed in dc, as shown in FIG. 4, where variation of the charge due to reduction of Fe(CN)$_6^{3-}$ traveling through the filter with 20-nm pores is given as a function of time. The accumulation of charge appears proportional to the square root of time, from where the net diffusion coefficient, D, can be estimated from the known concentration of Fe(CN)$_6^{3-}$ and the electrode area, A, using equation 1.

$$Q(t)=2AF[Fe(CN)_6^{3-}](Dt/\pi)^{1/2} \tag{1}$$

where F is the Faraday constant.

FIG. 4 shows a chronocoulometric plot for a charge passed through the modified nanoporous membrane with 20 nm pores modified with 21-mer ss-DNA before (A) and after (B) hybridization with the complementary 21-mer. Other conditions are similar to those in FIG. 4: 10 mM Fe(CN)$_6^{3-}$/10 mM Fe(CN)$_6^{4-}$ in 0.1 M KCl; 0 V versus Ag/AgCl.

Information on ion flow is conveniently illustrated through the frequency dependence of cell impedance, Z, measured at the half-wave voltage for the redox pair (0.22 V vs. Ag/AgCl).

Figure 5:
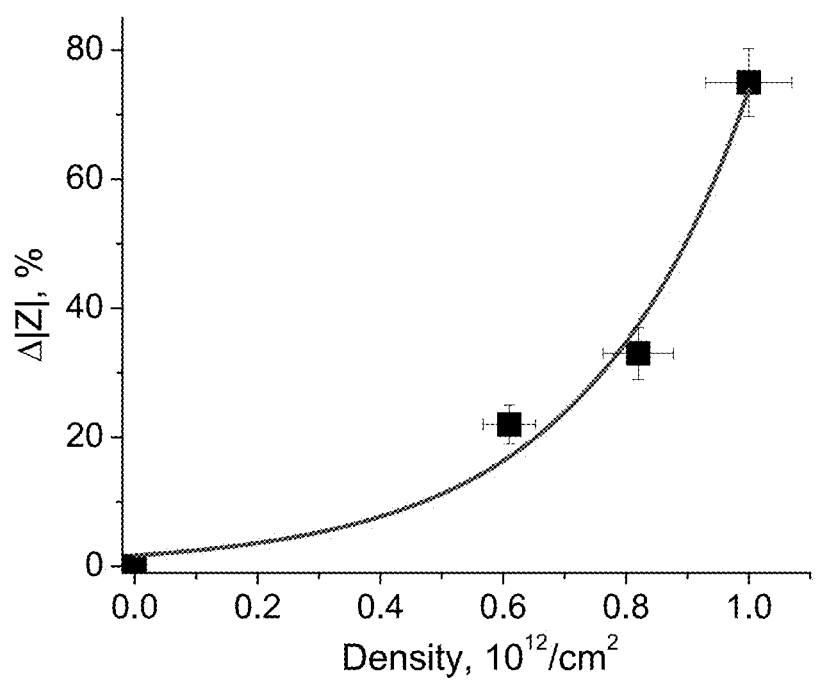
FIG. 5 shows the impedance increase at 0.01 Hz upon complete DNA hybridization as a function of surface density of initial ss-DNA.

The changes were observed with 20-nm pore membrane and not with the 200 nm. The impedance increases upon DNA hybridization similar to the decrease in the CV amplitude. The effect is dependent on the surface coverage of immobilized ss-DNA and the degree of its hybridization with target DNA, as illustrated by FIG. 5, where the impedance increase at 0.01 Hz is given as a function of surface density of initial ss-DNA upon complete target DNA hybridization. The solid line serves as a guide for the eye. The impedance increased nonlinearly with the surface concentration of ss-DNA upon "complete" hybridization (approximately 93% as judged by optical absorption) with the complementary 21-mer.

Example 2

1. Preparation of Membrane Substrates.

Highly ordered nanoporous aluminum oxide membranes were produced via a two-step anodization method as described by Li, A. P., et al., *J. Appl. Phys.*, 84, (1998), 6023; Masuda, H. and Fukuda, K., Science, 268, (1995), 1466, both references incorporated herein by reference. Briefly, aluminum foil (0.1 mm thick, Puratronic 99.997% aluminum) was first electropolished in an ethanol solution of HClO$_4$ then anodized in a 3% oxalic acid solution at a constant potential of 40 V for 3 hours at 7° C. The oxide layer was removed by a CrO$_3$—H$_3$PO$_4$ (1.8% CrO$_3$+6% H$_3$PO$_4$) solution, and the final anodization was performed under the same conditions to reach a desired pore length. Such a procedure yields hexagonally ordered nanopores of 60 nm diameter and 10 µm in length (after 3 hours of anodization). Hydrothermal treatment was carried out in boiling distilled water for different periods of time, causing the pores to shrink. The effect of shrinkage saturates after 40 minutes of boiling.

2. Electrochemical Measurements.

Electrical impedance was measured at 1 mV AC amplitude in the frequency range from 1 to 10$^5$ Hz using a CH Instrument 604B potentiostat in a cell using a two-electrode scheme with the back layer of aluminum under the membrane as a working electrode and a polished aluminum rod as the counter electrode immersed in electrolyte solution approximately 3 mm above the membrane. Solutions of KCl at various concentrations (from 10 mM to 3 M) at either pH=7.0 or in 0.1 M acetate buffer (pH=5.0) were used as electrolyte. The active membrane area was 0.79 cm$^2$.

Figure 6:
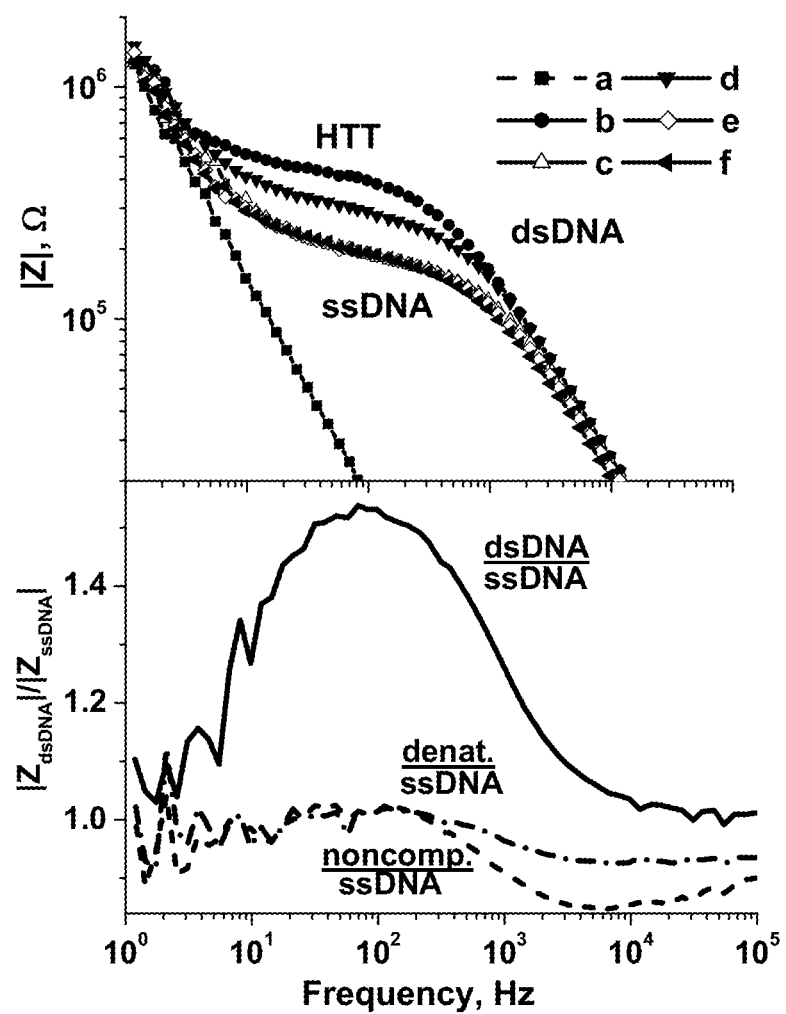
FIG. 6 shows (Top) an impedance Bode plot for nanoporous alumina membrane recorded in 0.1, M KCl solution: a—untreated membrane; b—membrane after hydrothermal treatment (HTT); c—HTT membrane after immobilization of ssDNA; d—after hybridization with complementary ssDNA; e—after dehybridization with urea; f—with noncomplementary ssDNA, and (Bottom) relative change of impedance after hybridizing with complementary (solid) and noncomplementary (dashed) analyte DNA; dot-dashed line shows the ratio for impedances before hybridization and after denaturing dsDNA with urea; the noise at low frequencies diminishes when higher AC amplitudes are used.

FIG. 6 illustrates the variation in the frequency dependent impedance (Bode plot) for the membrane before and after the hydrothermal treatment (HTT).

3. DNA Detection.

Immobilization of ssDNA inside shrunken nanopores leads to a significant decrease in the nanoporous membrane resistance (ssDNA) as compared to an unmodified hydrothermally treated membrane substrate.

Hybridization of immobilized ssDNA with a complementary strand leads to an increased membrane resistance (more than 50% in this example) with double stranded DNA (dsDNA), which nevertheless is lower than that without any DNA (HTT). The resistance is recovered upon denaturation in 9M urea and is not affected by a non-complementary sequence that does not hybridize.

With hydrothermally treated nanopores, the detection can be realized without a redox pair (i.e., using only electrolyte) and using aluminum electrodes.

One aspect of the present invention provides for detecting nucleic acid sequences (e.g. DNA or RNA) having a charged backbone structure upon their hybridization with a complimentary nucleic acid sequence having a neutral charge backbone structure (e.g. morpholino and peptide nucleic acid (PNA) sequences) bound to the surface of nanopores (also referred to herein as pores or nanochannels or channels), by measuring ionic conductance through the pores. The invention utilizes the surface charge mechanism as responsible for the ionic current change upon ligand-analyte binding. The technique can employ single nanopores or nanoporous membranes and can be extended to simultaneous measure of numerous nucleic acid sequence analytes. An additional advantage of using morpholinos and other non-naturally occurring nucleic acid sequence analogs (for e.g. PNAs) as ligands is their stability to enzymatic degradation and thus anticipated long shell life, as well as possibility for multiple reuses.

One embodiment of the present invention provides a nucleic acid sensor comprising one or more nanopores or assemblies of spaced nanopores in a nanoporous membrane and a detector for detecting a charged polynucleic acid sequence such as DNA or RNA in solution hybridizing with a ligand complimentary to the charged polynucleic acid sequence wherein the ligand complimentary to the charged polynucleic acid sequence is bound to the surface of the membrane lining the nanopore and wherein the surface bound ligand comprises a sequence of neutral analogs of nucleic acids or a morpholino and an electrode for measuring the ionic current change through the pores resulting from the complimentary binding. In one embodiment the nanopore diameter is greater than 10 nm (nanometers). In another embodiment the nanopore diameter is less than 500 nm. In a preferred embodiment, the membrane lining a nanopore may be modified with morpholino ligands (neutral analogs of DNA) designed to capture (hybridize with) complementary target polynucleic acid analyte from solution. In another preferred embodiment, the walls of nanopores are modified with morpholino ligands along with a neutral dilutant that does not participate in hybridizing with target polynucleic acid. In another preferred embodiment the walls of nanopores are modified with peptide nucleic acid ligands (neutral analogs of DNA) designed to capture (hybridize with) complementary target polynucleic acid analyte from solution. In a more preferred embodiment the walls of nanopores are modified with peptide nucleic acid ligands along with a neutral dilutant that does not participate in hybridizing with target polynucleic acid.

In a preferred embodiment, the electrodes are made of a noble metal such as gold, platinum or silver deposited on the nanopore walls at their entrance for measuring the (nonfaradeic) ionic current change. For example, the (nonfaradeic) ionic current change is measured in the AC (alternating current) mode. In a preferred embodiment, the electrodes are made of a nonpolarizable conducting material such as silver/silver chloride. In an alternative embodiment the ionic current change is measured in the DC (direct current) mode.

In an embodiment of the present invention, the ionic current at a low electrolyte concentration decreases as a result of hybridizing with the target polynucleic acid in the nanopores with the complementary ligands due to the surface charge effect. For example the ionic current change is measured on multiple electrodes with nanopores in between them modified with different ligands and thus allowing simultaneous detection of multiple targeted polynucleic acid sequences.

In one embodiment of the present invention, a "morpholino oligomer" or "morpholino" refers to a polymeric molecule having a backbone, preferably a neutral backbone, which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. In this embodiment, morpholinos are synthetic molecules which are the product of a redesign of natural nucleic acid structure. A morpholino oligomer can be about 25 bases in length, and can bind to complementary sequences of RNA by standard nucleic acid base-pairing. Structurally, the difference between morpholinos and DNA is that while morpholinos have standard nucleic acid bases, those bases are bound to morpholine rings instead of deoxyribose rings and linked through phosphorodiamidate groups instead of phosphates. Replacement of anionic phosphates with the uncharged phosphorodiamidate groups eliminates ionization in the usual physiological pH range, so morpholinos in organisms or cells are uncharged molecules. The entire backbone of a morpholino is made from these modified subunits. Morpholinos are most commonly used as single-stranded oligos, though heteroduplexes of a morpholino strand and a complementary DNA strand may be used in combination with cationic cytosolic delivery reagents.

Morpholinos are sometimes referred to as PMO (phosphorodiamidate morpholino oligo).

A preferred morpholino oligomer and or morpholino sequence is composed of one or more "morpholino subunit" structures, such as those shown below but not limited thereto, which in the oligomer and or sequence are preferably linked together by (thio)phosphorodiamidate linkages, joining the morpholino nitrogen of one subunit to the 5' exocyclic carbon of an adjacent subunit. Each subunit includes a purine or pyrimidine base-pairing moiety Pi which is effective to bind, by base-specific hydrogen bonding, to a base in a polynucleotide. An oligomer or sequence may be 1-5 units in length. In other embodiments, the oligomer or sequence may be 5-15, 15-25, 25-50, 50-100 or longer subunits in length.

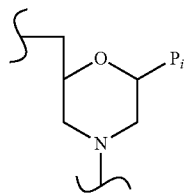

In another embodiment of the present invention, a thiophosphorodiamidate linkage contains an oxygen atom, typically an oxygen pendant to the backbone in the oligomers described herein, is replaced with sulfur.

According to another embodiment of the present invention, an "activated phosphoramidate group" is typically a chlorophosphoramidate group, having substitution at nitrogen which is desired in the eventual phosphoramidate linkage in the oligomer. An example is (dimethylamino)chlorophosphoramidate, i.e. —O—P(.═O)(NMe$_2$)Cl.

According to another embodiment of the present invention, the terms "charged", and "uncharged", as used herein refer to the predominant state of a chemical moiety at near-neutral pH, e.g. about 6 to 8. Preferably, the term refers to the predominant state of the chemical moiety at physiological pH, i.e. about 7.4.

In yet another embodiment of the present invention, a "phosphorodiamidate" group comprises phosphorus having two attached oxygen atoms and two attached nitrogen atoms, and herein may also refer to phosphorus having one attached oxygen atom and three attached nitrogen atoms. In the inter-subunit linkages of the oligomers described herein, one nitrogen is typically pendant to the backbone chain, and the second nitrogen is the ring nitrogen in a morpholino ring structure, as shown in formula II below. Alternatively or in addition, a nitrogen may be present at the 5'-exocyclic carbon, as shown in formulas III and IV below.

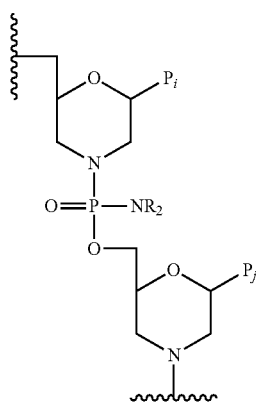

II

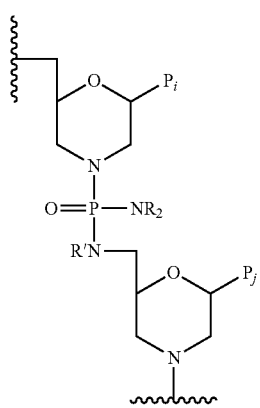

III

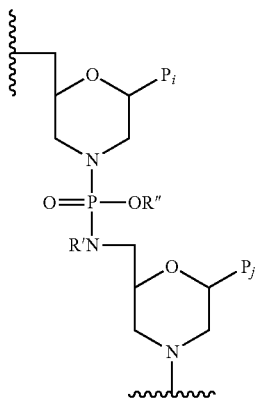

IV

Examples of morpholino oligomers are illustrated in, for example, U.S. Pat. Nos. 5,698,685, 5,217,866, 5,142,047, 5,034,506, 5,166,315, 5,185,444, 5,521,063, and 5,506,337, all of which are expressly incorporated by reference herein.

According to another embodiment of the present invention, peptide nucleic acids (PNA(s)) backbone is composed of repeating N-(2-aminoethyl)-glycine units linked by peptide bonds. The various purine and pyrimidine bases are linked to the backbone by methylene carbonyl bonds. PNAs are depicted like peptides, with the N-terminus at the first (left) position and the C-terminus at the right. Peptide nucleic acid (PNA) is a DNA analogue in which the phosphodiester backbone has been replaced by a synthetic peptide backbone that is neutral and achiral.

According to one embodiment of the present invention, the surface charge effect can be utilized for analyte (e.g. DNA) sensing in nanopores of a diameter larger than the volume exclusion mechanism required. Opposite to the volume exclusion mechanism, low ionic strengths and neutral nucleic acid sequences (e.g. neutral DNA analogs) as capturing elements/ligands on nanopore surface are preferred for illustration of the surface charge method. When the bulk concentration of electrolyte is low, surface charge on the walls of the nanochannel dictates the concentration of ions inside the nanochannel and causes the ionic conductance to become independent of the bulk concentration. To fulfill electroneutrality, the nanochannel is filled predominantly with ions having an opposite charge to that of the wall surface. If an analyte such as DNA binds to the wall, it changes the surface charge and thus the ionic concentration and conductance through the nanochannel. Unlike the volume exclusion regime, binding of a charged analyte alters the conductance even if the overall cross section of the nanopore is barely changed.

Even when the radius of a nanochannel, a, is larger than the Debye length, $r_D$, defined by the bulk ion concentration, $C_{bulk}$ (monovalent in this case)

$$\frac{1}{r_D} = \left[\frac{2e^2 C_{bulk}}{\varepsilon_o \varepsilon k_B T}\right]^{1/2} \quad (2)$$

the ions of the same charge as that of the walls are appreciably expelled from the nanochannel, and the electrical current through the nanochannel is primarily carried by the ions of the opposite charge. From the electroneutrality requirement, the difference between the concentrations of oppositely charged monovalent ions of the electrolyte, ΔC, is defined by the surface charge density, σ, and the nanochannel radius, a:

$$\Delta C = \frac{2\sigma}{ea} \quad (3)$$

It is convenient in some cases to express the charge density via the surface density of monovalent charges, $\sigma = eN_s$.

In one embodiment of the present invention, if the positive and negative ions of the electrolyte have the same diffusion constant, D (which is very close in the case of KCl) and it is presumed to be unaltered inside the small diameter nanochannel, the ionic current through a single cylindrical nanochannel of length L under applied voltage V can be expressed as $$I_{channel} = \frac{e^2 \pi a^2}{k_B T} \frac{D\sqrt{\Delta C^2 + 4C_{bulk}^2}\, V}{L} \quad (4)$$

A membrane of the cross section area A consists of an array of multiple nanochannels in parallel, thus making its porosity (a fraction of the cross section that is empty) equal to $\alpha$, has the resistance $$Z_{mem} = \frac{k_B T}{e^2 \alpha D \sqrt{\Delta C^2 + 4C_{bulk}^2}} \frac{L}{A}. \quad (8)$$

It is almost identical to that of the unhindered solution of the same dimensions, $Z_{sol}$, only for $C_{bulk} \gg \Delta C$. In the opposite limit, $\Delta C \gg C_{bulk}$, $Z_{mem}$ becomes less than $Z_{sol}$ and independent of $C_{bulk}$. The difference in these resistances, according to eq. 5, can be quite significant and can be utilized with appropriately designed ligands placed inside the nanochannels. It is desirable to have the electrodes as close as possible to the pores so that the electrolyte resistance outside the pores has minimal effect. Because of a low electrolyte concentration necessary for this detection scheme, nonpolarizable electrodes, such as AgCl, are not applicable and faradeic currents would be difficult to control as well. The best configuration employs the AC mode of measurement with noble electrodes such as gold that have large double layer capacitance and are directly deposited on the opposite sides of the membrane.

Figure 7:
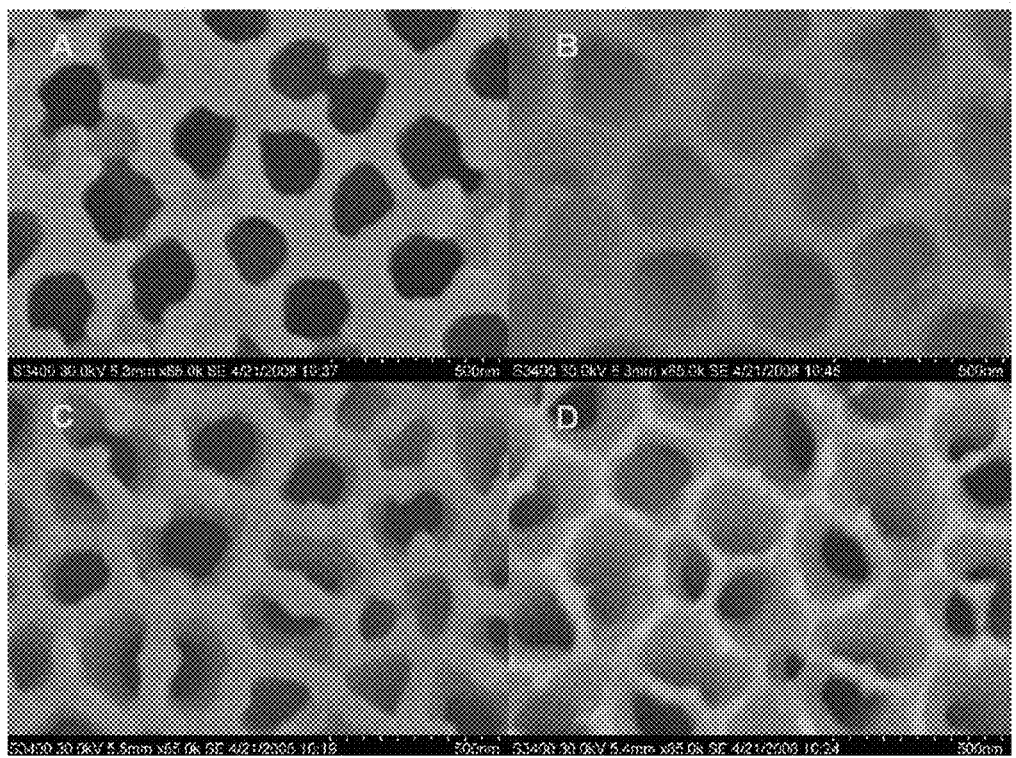
FIG. 7 shows SEM images of the opposite sides of a commercially available (Whatman) anodized aluminum oxide (AAO) membrane with about 200 nm nominal diameter before (A and B) and after (C and D) the deposition of about 200 nm gold.
Figure 8:
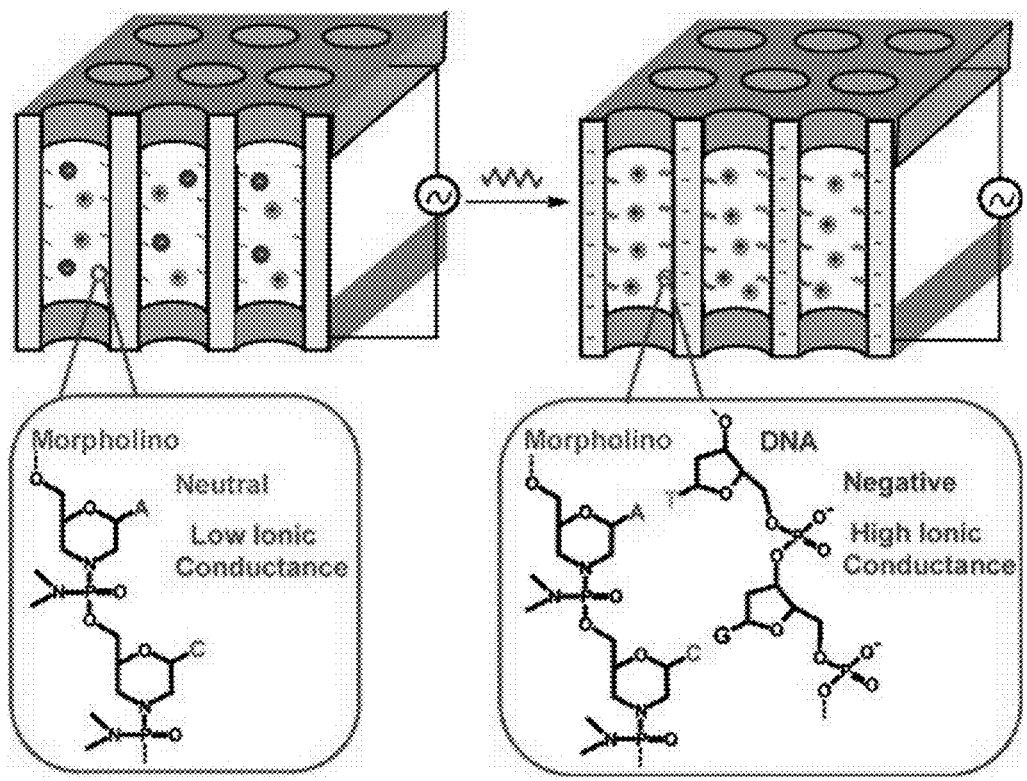
FIG. 8 illustrates an embodiment of the present invention comprising a sensor with gold electrodes on the opposite sides of a nanoporous membrane the internal walls of which are modified with a morpholino oligonucleotide; its hybridization with DNA analyte is detected as increase of ionic conductance through the membrane at low electrolyte concentration.

According to one embodiment of the present invention, the frequency dependence of the sensor (membrane) impedance, $|Z_{mem}|$ is defined by the cell parameters, such as pore diameter and length, concentrations of electrolyte (as shown in eq. 5), membrane capacitance, and the electrode capacitance, $C_{dl}$, and resistance, $R_{el}$. The optimal frequency of measurements and electrolyte concentration are chosen in such a way as to maximize the resistive contribution of the membrane pores, $R_p$, to $|Z_{mem}|$. The latter is seen in the Bode plot (see FIG. 9), as an almost horizontal part in the frequency dependence. In one embodiment presented here, the electrodes are placed directly at the membrane, which eliminates the contribution to the resistance from solution outside the pores and leaves only the electronic resistance of the gold electrodes, which is still noticeable because of the small thickness and narrow reams of the resulting electrode mesh (see FIGS. 7 and 8). At high frequencies and high electrolyte concentrations, the membrane capacitance, $C_p$, is barely recognizable in the Bode plots (one can identify it at low electrolyte concentrations as a dip at high frequencies). The impedance of the double layer capacitance, $C_{dl}$, arises as a low frequency impedance rise inversely proportional to frequency. Its value has contributions from both the Helmholtz layer, $C_H$, and the diffusive layer, $C_{dif}$:

$$\frac{1}{C_{dl}} = \frac{1}{C_H} + \frac{1}{C_{dif}} \quad (6)$$

Figure 9:
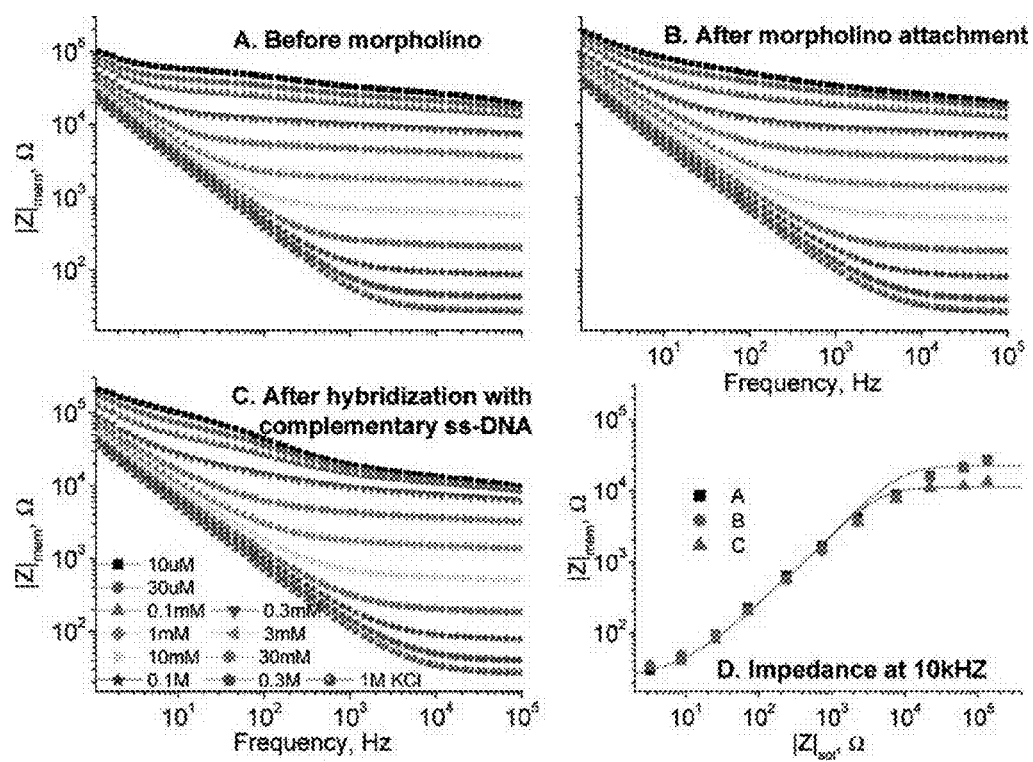
FIG. 9 shows Bode plots at different concentrations of KCl for the membrane modified with aminosilane (for 1 h) and activated by gluteraldehyde (A); the same membrane after immobilization of the morpholino (B) and after hybridizing with complimentary target cDNA 15-mer (C). (D) Impedance at about 10 kHz for membranes of A (■) and B (●) and C (▲) as functions of the KCl concentration measured as the impedance of free solution. The solid lines represent the best fits with $R_{ef}$=about 22Ω and the surface charge densities, the concentration jump, $\Delta C$=about $4.8 \times 10^{-4}$ M (red) and about $9.5 \times 10^{-4}$ M (green).

The latter causes the concentration dependence of $C_{bulk}$ ($C_{dif} \sim C_{bulk}^{1/2}$), which is visible in FIG. 9. The membrane pore resistance responsible for the frequency independent part of $|Z_{mem}|$ in FIG. 9 has a close to linear dependence on the electrolyte concentration. This optimal frequency for this embodiment is in the range 1-30 kHz. FIG. 9D presents it as a function of the free solution impedance, $|Z_{sol}|$. The saturation at low $|Z_{sol}|$ (high electrolyte concentration, $C_{bulk}$) is due to the electrode resistance, which is on the order of 20Ω. Variation of $|Z_{mem}|$ at low $C_{bulk}$ (high $|Z_{sol}|$) is due to the surface charge effect and is the basis of DNA sensing. FIG. 9B illustrates that Bode plots for the membrane modified with covalently bound to its surface single-stranded neutral analog of DNA (e.g. morpholino) which has a distinctly different resistances at low electrolyte concentrations from that of FIG. 9C with the complimentary DNA hybridized onto morpholino, which is the result of a higher surface charge brought about by DNA. The effect is clearly visible in FIG. 9D, where $|Z_{mem}|$ at about 10 kHz is plotted versus $|Z_{sol}|$ for membranes with and without DNA. The membrane with covalently attached to neutral analogues of DNA, morpholino, which are used as surface bound ligands to capture target DNA analytes from solution. Because of the neutral charge, the morpholino analogue of polynucleic acid is a preferred ligand to capture target ss-DNA: it contributes zero charge to the surface and its hybridization with cDNA is practically independent of the salt concentration.

At low ionic strengths (high $|Z_{sol}|$) the membrane resistance, presented as the impedance at 10 kHz, $|Z_{mem}|$ is lower than that of the unrestrained solution not only for the membrane after hybridization with cDNA but also, to a lower extent, for the membrane before DNA binding as well (see FIG. 9D). The effective surface charge densities, measured as the $\Delta C$ value, are $\Delta C$=approximately $9.5 \times 10^{-4}$ and approximately $4.8 \times 10^{-4}$ M for the two cases respectively. Even when neutral DNA analog is used, there is often a nonzero surface charge in both cases. Alumina surface has PZC (point of zero charge) exceeding pH >8.5 and thus is positively charged at neutral pH. Residual alumina hydroxyls, as well as amino groups from the surface modification, render the surface positively charged. Even if the surface is modified by ester silane, to render the surface neutral, the surface charge does not totally disappear and retains residual charge about 25% of the original value, as judged by the value and sign of the streaming potential. The streaming potential arises from electrolyte moving in the pore under the pressure gradient and gains the value proportional to the surface charge density if the velocity profile of the liquid is the same. Upon amination with only APTS (3-aminopropyltrimethoxysilane, from Aldrich), the streaming potential increases slightly because of similar charge densities of hydroxyl groups on alumina and attached amino groups. When the surface amines are activated by gluteraldehyde, the streaming potential also does not change because the resulting Schiff base is still charged. Upon DNA attachment, on the other hand, the amount of positive charge decreases and its sign can change if a significant portion of the activated groups are utilized for DNA binding. The density of immobilized aminated DNA is much less than the density of the surface amines. It was observed in one embodiment of the present invention that the maximum density of bound ss-DNA 21-mer did not exceed $10^{13}/cm^2$. Thus, the charge of fully aminated surface (with the surface density on the order of $3 \times 10^{14}/cm^2$) decreases upon DNA binding. For that reason, the amination in FIG. 9 was performed for about 1 h because not all amines were employed for DNA immobilization.

Figure 10:
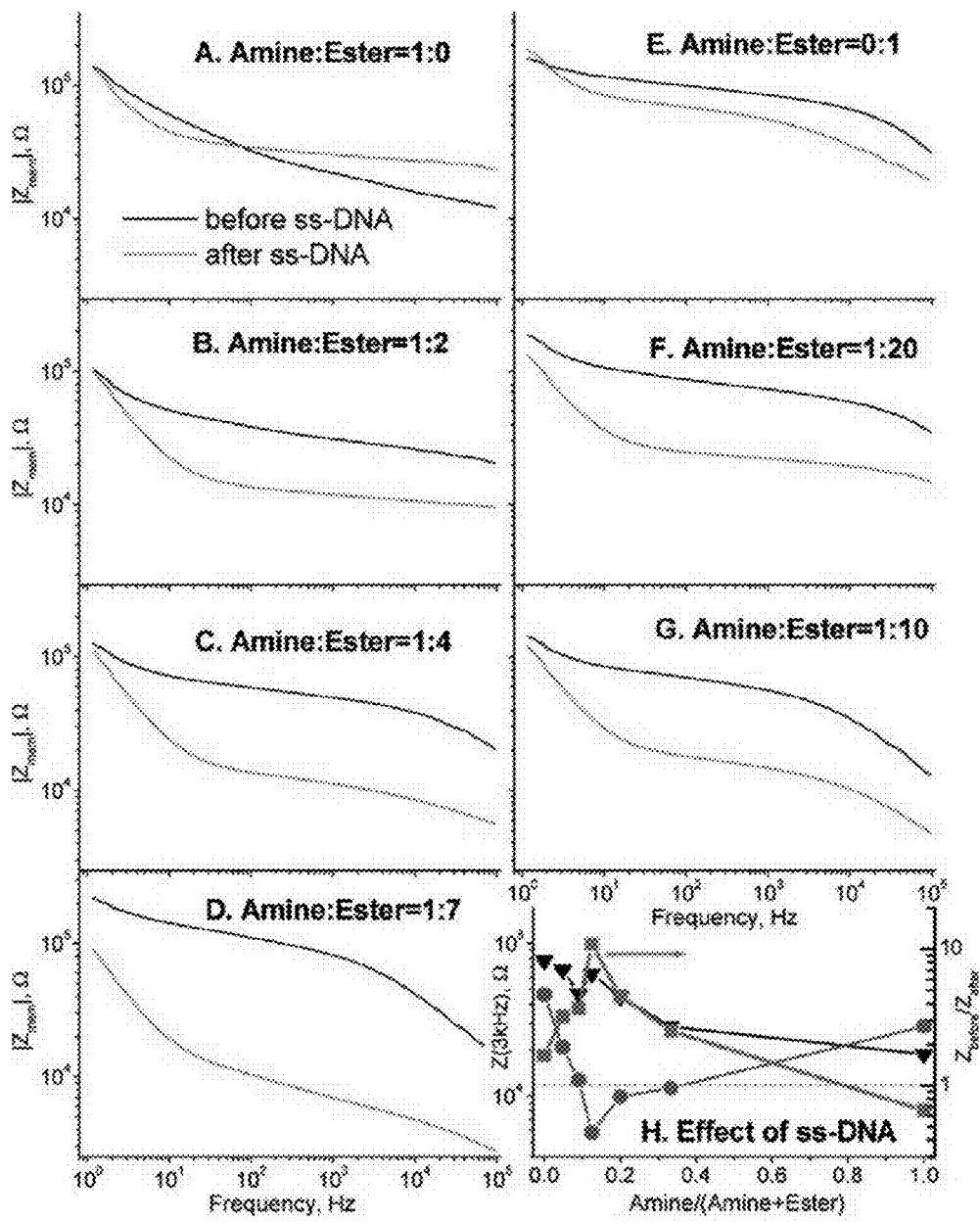
FIG. 10 illustrates the sensor optimization in choosing appropriate ratio of amine/ester silanes for the maximum response after DNA binding on amines. Bode plots for ionic conductance (at about 10 μM of KCl) through the membranes before (black) and after (red) immobilization of ss-DNA (16-mer). Different relative concentrations of the amine and ester (A-G) result in different surface densities of DNA. The effect of DNA binding, shown in H, as the ratio (red squares) of the impedance at approximately 3 kHz before (black triangles) and after DNA binding (blue circles), has the optimal amine/ester ratio for maximal effect near amine/ester=1:7, as in D. Note that, for the surface with maximum amount of amines, the impedance increases after DNA binding.

In an embodiment of the present invention, the sensor can be optimized for improved response to DNA by preparing mixed surface modifications, where amino silanes are diluted by ester silanes. Since not all of the amines can subsequently bind DNA or morpholino, the amount of amines has an optimum. The silanization process in this case was performed with different silane mixtures for about 12 h. FIG. 10 illustrates that the membrane with 100% aminated surface shows the lowest resistance, which increases upon DNA binding due to decreasing of the total charge. Mixed amino/ester silane modifications produce fewer amines and thus fewer of them are left unreacted after DNA immobilization. Increasing the proportion of neutral ester in the modifications increases the membrane resistance before DNA binding; it also causes the effect of the resistance drop upon DNA binding to enhance. Eventually, at very low fractions of amine, the amount of bound ss-DNA becomes insufficient to induce the surface charge change greater than the residual charge, and the effect of resistance change upon DNA binding declines again.

FIG. 10H suggests that a preferred fraction of aminosilane is approximately 1:7 for this choice of the material (alumina) and the pore diameter (nominal diameter of about 200 nm). The corresponding conductance enhancement is close to approximately 10 according to one embodiment of the present invention. The theoretical surface charge enhancement for replacing one positive charge of amine by a 15-mer DNA oligomer is 13 (15 nucleobases minus 2 Schiff bases from gluteraldehyde), which is in a remarkably good agreement with the observed factor of 10.

Figure 11:
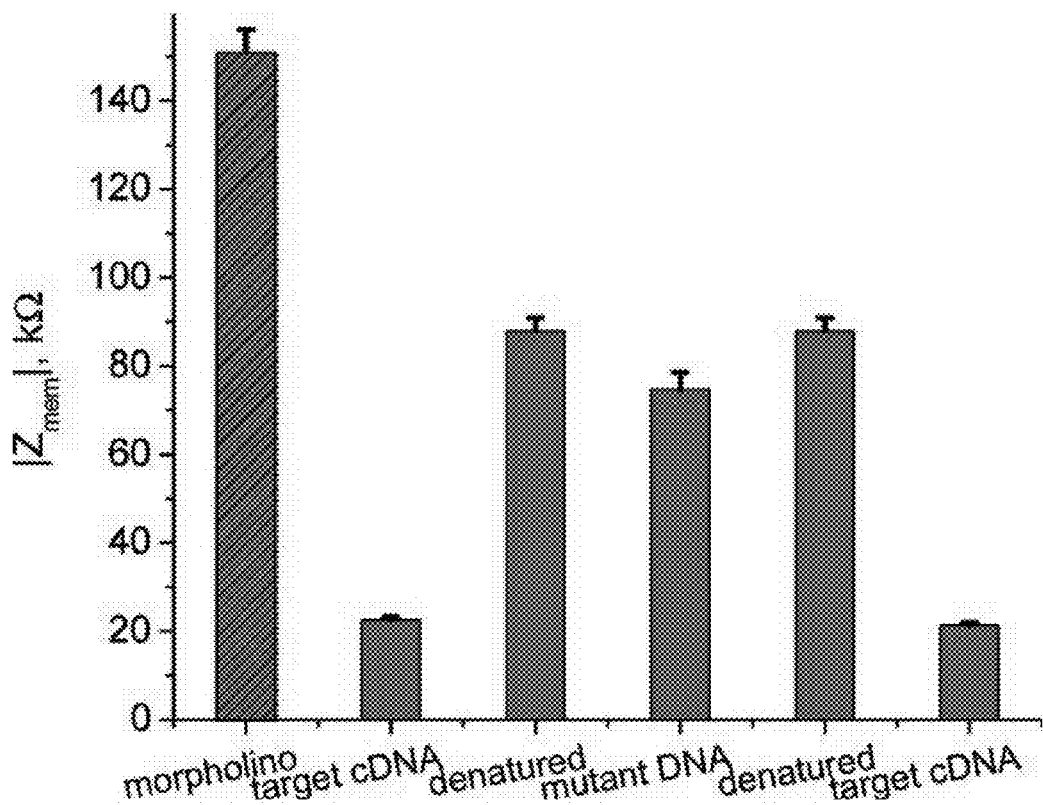
FIG. 11 shows ionic impedance at approximately 3 kHz through the morpholino modified membrane prepared with the 1:7 ratio of amine/ester silanes. Different stages of DNA sensing are shown, where target and mutant are the complimentary and non-complimentary 15-mer DNA oligomers, respectively. The measurements were performed in 10 μM KCl buffer, and denaturing was achieved with 9.0 M urea.

In an example, this ratio amine/ester is about 1:7 was used in construction of improved DNA sensor, where the same morpholino as in FIG. 9 was immobilized on activated by gluteraldehyde silanized surface. Referring now to FIG. 11, the resistance changes at about 3 kHz in the course of hybridization/denaturing with the complimentary and mutant target DNA, according to one embodiment of the present invention. When compared with the morpholino modified membrane, the resistant at first drops over 7-fold after hybridization with the complimentary strand, but when compared with the value after denaturing, the effect is only about 4-fold. Even with that incomplete recovery after denaturing, the effect is still significantly larger than that in FIG. 9. Hybridization with a noncomplimentary DNA, on the other hand, barely changes the membrane resistance as compared with the value after denaturing. The overall effect of the resistance change with complimentary DNA is greater than in FIG. 9.

One aspect of one embodiment of the present invention provides that the surface charge effect in controlling the ionic conductance through a nanoporous alumina membrane can be applied as a convenient detection method for unlabeled DNA. The method was realized on the membranes with gold electrodes deposited directly on its opposite sides and the surface of nanopores modified by an optimized mixture of neutral ester silanes and morpholinos (neutral analogue of DNA). Another aspect of the present invention provides that the surface charge effect can be employed in fabrication of inexpensive electrical DNA sensors. Such a sensor would not require an electrochemical potentiostat and can be eventually employed with standard interfaces available on every computer.

Embodiments of the present invention are further illustrated by the following non-limiting examples for detection of genetic mutation related to cystic fibrosis.

Example 3

Cystic fibrosis transmembrane conductance regulator (CFTR) is a protein responsible for transport of chloride ions across the membranes of cells in the lungs, liver, pancreas, digestive tract, reproductive tract, and skin. Genetic mutations observed in about 70% of patients with cystic fibrosis (CF) result from deletion of three base pairs in CFTR's nucleotide sequence. This deletion causes loss of the amino acid phenylalanine located at position 508 in the protein; therefore, this mutation is referred to as ΔF508 or F508. CFTR protein with the ΔF508 mutation is incorrectly folded and prevents it from reaching the cell membrane. People who are homozygous for this mutation tend to have the most severe symptoms of cystic fibrosis due to critical loss of chloride ion transport which accounts for more than 90% of the clinical cases. The sodium and chloride ion imbalance creates a thick, sticky mucus layer that cannot be removed by cilia and traps bacteria, resulting in chronic infections. Because of a dramatic mutation, the difference in melting temperatures for a short DNA oligo near the mutation site with complimentary, cDNA, and the mutant target DNA, mDNA, is significant, especially with morpholino. The correct CFTR sequence near the mutation site, ATC ATC TTT GGT GTT (SEQ ID NO:4) has a melting temperature, Tm, even with the complimentary 15-mer "ligand" DNA, AAC ACC AAA GAT GAT (SEQ ID NO:5), of around $T_m \sim 45°$ C. The mutant DNA of the same length (with truncated CTT), ATC ATT GGT GTT TCC (SEQ ID NO:6), has $T_m < 25°$ C. The difference is even more dramatic with morpholino/DNA pairs. These DNA sequences were used as complimentary and noncomplimentary DNA analytes in FIGS. 9-11.

Details of Preparation and Experimental Conditions.
1. Surface Modification.

Anodized alumina membranes (AAO) from Whatman with the nominal diameter of approximately 200 nm and an approximately 60 μm thickness were boiled in water and dried in an oven at about 120° C. before modification. The membranes were first modified with ethanol solution of silanes. Either sole APTS (3-aminopropyltrimethoxysilane, from Aldrich) or its mixture with ETS (2-(carbomethoxy) ethyltrichlorosilane, from Gelest) in different proportions (APTS/ETS=0:1, 1:20, 1:10, 1:7, 1:4, 1:2) was used. The amount of ester silane, ETS, in the mixtures was fixed at about 2 w/v %, and the amount of APTS was varied to achieve the desired ratio. Two options were tried: about 1 h of silanization by aminosilane and overnight silanization with the mixtures (including those of sole aminosilane and sole ester silane). After washing with ethanol, the membranes were baked at about 120° C. for about 3 h to ensure the completion of covalent linkage of silanes to the surface and their lateral polymerization in the monolayer. The remaining modifications (originating on the surface-bound amines) were performed after deposition of gold electrodes on the membrane and after placing it inside the cell.
2. Cell Assembly and Impedance Measurements.

Gold electrodes (200 nm Au on 3 nm Cr underlayer) were deposited on opposite sides of the membrane using a Gatan Ion Beam Coater (681 Series) at about 15° angle to the normal of the membrane. The thickness and the angle of deposition were optimized initially to minimize the electrode electrical resistance and to increase their surface area necessary for lowering the electrode impedance.

The surface of each membrane was activated by overnight treatment in 5% aqueous solution of glutaraldehyde (Aldrich). After drying by nitrogen gas, the membrane was assembled into the cell, where the remaining modifications were performed. The homemade cell held the modified membrane between the two PMMA pieces (sealed by parafilm) with matching holes for solution flow. The holes identified three independent regions for conductance measurements each with about a 1.5 mm diameter. The corresponding electrodes on the opposite sides of the membrane were connected to a potentiostat (700C series, from CH Instruments) for impedance measurements that were performed in the two-electrode scheme under small AC voltage (≤10 mV) (see for example Scheme 1).

The Bode plots in the frequency range from 1 to $10^5$ Hz were collected about 90 min after the last manipulation with solution exchange. Separate measurements confirmed that to be sufficient for the signal stabilization. Various concentrations of KCl in DI water ranging from about 10 µM up to about 1 M were used to confirm the manifestation of the surface charge effect. The solutions were equilibrated with air to avoid variations due to dissolution of carbon dioxide; their pH was about 5.5. The resistances of these solutions were also measured in a separate conductivity cell with platinum electrodes and the cell constant equaled about 0.3 cm$^{-1}$. The experiments for DNA detection were typically performed at about 10 µM KCl.

3. Immobilization of Nucleic Acids.

Aminated nucleic acids were immobilized on the aldehyde activated membrane surfaces that are already placed inside the cell. Approximately 30 µL of ~100 µM solution of aminated nucleic acid (5'-aminated morpholino or 5'-aminated DNA) in DI water (Milli-Q) was injected into the cell and left overnight under a seal preventing water from evaporation. After that, the membrane was washed with about 0.1 M KCl and, finally, with copious amounts of DI water.

4. Hybridization and Denaturing Procedures.

Hybridization was typically performed by ~5 µM of DNA in PBS (0.1 M KCl) at room temperature for approximately 1 h. The unhybridized DNA was washed off from the membrane by copious amounts of solution to be measured in (typically about 10 µM KCl). The denaturation was achieved by treatment with about 9 M urea, which included about 1 h soaking and washing with copious amounts. The treatment was finished by washing with copious amounts of the solution used in measurements.

5. Nucleic Acids.

All DNA oligomers were ordered from Integrated DNA Technologies (Coralville, Iowa) of HPLC purified quality and used without further purification. All sequences are given starting from 5'. The surface-bound aminated DNA (/5AmMC6/AAC ACC AAA GAT AAT A (SEQ ID NO:7)), its complimentary target cDNA (ATC ATC TTT GGT GTT (SEQ ID NO:4), and the mutant target mDNA (ATC ATT GGT GTT TCC (SEQ ID NO:6)) represent a normal and the genetic mutation sequences for cystic fibrosis. The amino modification is shown between slashes.

A neutral analogue of polynucleic acid oligomer, morpholino oligo, has morpholine rings instead of the deoxyribose sugar moieties connected by nonionic phosphorodiamidate linkages replacing the anionic phosphates of DNA. Each morpholine ring attaches one of the standard DNA bases. Aminated at 5' morpholino, /5AmMC6/TTT TTT AAC ACC AAA GAT GAT (SEQ ID NO:8), was ordered from Gene Tools LLC (Philomath, Oreg.). It represents a truncated 12-mer portion of the above-described aminated DNA that has a six-thymine extension. Some experiments were also performed with an analogous aminated DNA 21-mer, /5AmMC6/TTT TTT AAC ACC AAA GAT GAT (SEQ ID NO:8). The amino modification is shown between slashes.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above, and of the corresponding application(s), are hereby incorporated by reference.

What is claimed is:

1. A method for detecting biological analytes comprising a nucleic acid sequence with a charged backbone using ionic conductance through one or more nano-sized pores, the method comprising:
   providing a nanoporous membrane substrate having one or more nano-sized pores;
   covalently binding onto a wall of the one or more nano-sized pores a capturing element comprising a morpholino oligonucleotide and/or a peptide nucleic acid oligonucleotide, wherein the morpholino and/or PNA oligonucleotide comprises a neutral charged backbone structure;
   exposing the capturing element that is covalently bound onto the wall of the one or more nano-sized pores to a solution possessing the biological analytes, wherein the biological analytes are complementary to the capturing element and require no modification so that biological complementary analytes specifically bind to the capturing element and alter the surface charge of the nanopore; and
   exposing the one or more nano-sized pores bulk concentration of electrolytes low enough so that the surface charge on walls of the one or more nano-sized pores dictates the concentration of ions inside the one or more nano-sized pores and causes the ionic conductance to become independent of the bulk concentration of electrolytes; low concentration of electrolytes;
   detecting a change of ion concentration as a result of ions being carried through the one or more nano-sized pores being of opposite charge as the charge of the wall of the one or more nano-sized pores and thus realizing an increase of ionic conductance through the one or more nano-sized pores upon specific binding of the capturing element and the biological complementary analytes.

2. The method of claim 1 wherein the biological analytes are selected from the group consisting of an enzyme, a nucleic acid, a virus, an antigen, an antibody, and a combination thereof.

3. The method of claim 1 wherein the nanoporous membrane substrate comprises an oxide surface.

4. The method of claim 1 wherein at least a portion of the one or more nano-sized pores comprises a diameter of 200 nm or less.

5. The method of claim 1 further comprising simultaneously detecting different species of the biological analytes by modifying the nanoporous membrane substrate with different morpholinos.

6. The method of claim 1 further comprising hydrothermally treating the nanoporous membrane substrate for narrowing diameters of the nano-sized pores and increasing resistance through the nano-sized pores.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Completely Synthesized Surface Bound 21-mer

<400> SEQUENCE: 1
gcttaggatc atcgaggtcc a                                              21

<210> SEQ ID NO 2
<211> LENGTH: 21
<212> TYPE: DNA
<213> ORGANISM: Artificial Sequence
<220> FEATURE:
<223> OTHER INFORMATION: Completely Synthesized Complement 21-mer

<400> SEQUENCE: 2
```
tggacctcga tgatcctaag c                                      21

<210> SEQ ID NO 3
<211> LENGTH: 21
<212> TYPE: DNA
<213> ORGANISM: Artificial Sequence
<220> FEATURE:
<223> OTHER INFORMATION: Completely Synthesized 21-mer

<400> SEQUENCE: 3
ggccttaatc ggatagagtg a                                      21

<210> SEQ ID NO 4
<211> LENGTH: 15
<212> TYPE: DNA
<213> ORGANISM: Artificial sequence
<220> FEATURE:
<223> OTHER INFORMATION: CFTR sequence near the mutation site

<400> SEQUENCE: 4
atcatctttg gtgtt                                             15

<210> SEQ ID NO 5
<211> LENGTH: 15
<212> TYPE: DNA
<213> ORGANISM: Artificial sequence
<220> FEATURE:
<223> OTHER INFORMATION: Complimentary 15-mer "ligand" DNA

<400> SEQUENCE: 5
aacaccaaag atgat                                             15

<210> SEQ ID NO 6
<211> LENGTH: 15
<212> TYPE: DNA
<213> ORGANISM: Artificial sequence
<220> FEATURE:
<223> OTHER INFORMATION: Mutant DNA of the same length (with truncated
      CTT)

<400> SEQUENCE: 6
atcattggtg tttcc                                             15

<210> SEQ ID NO 7
<211> LENGTH: 16
<212> TYPE: DNA
<213> ORGANISM: Artificial sequence
<220> FEATURE:
<223> OTHER INFORMATION: Surface-bound aminated DNA

<400> SEQUENCE: 7
aacaccaaag ataata                                            16

<210> SEQ ID NO 8
<211> LENGTH: 21
<212> TYPE: DNA
<213> ORGANISM: Artificial sequence
<220> FEATURE:
<223> OTHER INFORMATION: Aminated at 5' morpholino

<400> SEQUENCE: 8 tttttttaaca ccaaagatga t                                     21